(12) United States Patent
Blank et al.

(10) Patent No.: US 10,233,262 B2
(45) Date of Patent: Mar. 19, 2019

(54) GLYCAN ANALYSIS

(71) Applicant: ACADEMISCH ZIEKENHUIS LEIDEN, Leiden (NL)

(72) Inventors: Dennis Blank, Biberach (DE); Manfred Wuhrer, Voorschoten (NL); Karli Robert Reiding, The Hague (NL)

(73) Assignee: ACADEMISCH ZIEKENHUIS LEIDEN, Leiden (NL)

( * ) Notice: Subject to any disclaimer, the term of this patent is extended or adjusted under 35 U.S.C. 154(b) by 330 days.

(21) Appl. No.: 15/038,423

(22) PCT Filed: Nov. 20, 2014

(86) PCT No.: PCT/EP2014/075189
§ 371 (c)(1),
(2) Date: May 20, 2016

(87) PCT Pub. No.: WO2015/075139
PCT Pub. Date: May 28, 2015

(65) Prior Publication Data
US 2016/0289346 A1 Oct. 6, 2016

(30) Foreign Application Priority Data

Nov. 21, 2013 (GB) .................................. 1320571.1

(51) Int. Cl.
*C08B 37/00* (2006.01)
*G01N 21/64* (2006.01)
*H01J 49/00* (2006.01)
*H01J 49/16* (2006.01)
*H01J 49/40* (2006.01)

(52) U.S. Cl.
CPC ..... *C08B 37/0006* (2013.01); *G01N 21/6428* (2013.01); *H01J 49/0027* (2013.01); *H01J 49/164* (2013.01); *H01J 49/40* (2013.01)

(58) Field of Classification Search
None
See application file for complete search history.

(56) References Cited

FOREIGN PATENT DOCUMENTS

| CN | 102239173 A | 11/2011 |
| CN | 102574930 A | 7/2012 |
| CN | 103301472 A | 9/2013 |
| EP | 2 358 731 A2 | 8/2011 |
| EP | 2 484 699 B1 | 8/2012 |

OTHER PUBLICATIONS

Wheeler, Rapid Commun. Mass Spectrom. 2009; 23: 303-312.*
Rydergren, Chemical Modifications of Hyaluronan using DMTMM-Activated Amidation, Uppsala Universitet, Aug. 2013.*
Shah, Anal Chem. Apr. 2, 2013; 85(7): 3606-3613.*
Chan, J. Org. Chem. 2007, 72, 8863-8869.*
Ruhrik, Anal Bioanal Chem (2010) 397:3457-3481.*
Alley et al., "Glycomic Analysis of Sialic Acid Linkages in Glycans Derived from Blood Serum Glycoprotein", Journal Of Proteome Research, vol. 9(6), p. 3062-3072, (2010).
Harvey, "Derivatization of Carbohydrates for Analysis by Chromatography; Electrophoresis and Mass Spectrometry," J Chromatogr B Analyt Technol Biomed Life Sci., vol. 879(17-18), p. 1196-1225, (2011); Abstract Only.
International Search Report of International Application No. PCT/EP2014/075189, dated Feb. 9, 2015, 4 pages.
Konig et al., "Eine neue Methode zur Synthese Von Peptiden: Aktivierung Der Carboxylgruppe Mit Dicyclohexylcarbodiimid Unter Zusatz Von 1-Hydroxy-Benzotriazole A New Method for Synthesis of Peptides: Activation of the Carboxyl Group With Dicyclohexylcarbodiimide Using 1-Hydroxybenzotriazoles As Additives", Chemische Bericht, vol. 103, p. 788-798, (1970). (German Translation Only.).
Liu et al., "Methylamidation for Sialoglycomics by MALDI-MS: A Facile Derivatization Strategy for Both alpha2-3 and alpha2, 6-Linked Sialic Acids", Anal. Chem. vol. 82, p. 8300-8306, (2010).
Miura et al., "Rapid and Simple Solid-Phase Esterification of Sialic Acid Residues for Quantitative Glycomics by Mass Spectrometry", Chem. Eur. J., vol. 13, p. 4797-4804, (2007).
Neises et al., "Simple Method for the Esterification of Carboxylic Acids", Angew. Chem. Intl Ed. Engl., vol. 17(7), p. 522-524, (1978).
Powell et al., "Stabilization of Sialic Acids in N-linked Oligosaccharides and Gangliosides for Analysis by Positive Ion Matrix-assisted Laser Desorption/ionization mass spectrometry," vol. 10(9), p. 1027-1032, (1996), Abstract Only.
Ruhaak et al., "Glycan labeling strategies and their use in identification And quantification", Analytical and Bioanalytical Chemistry, vol. 397(8), p. 3457-3481, (2010).
Tep et al., "A MALDI-TOF MS method for the simultaneous and quantitive analysis of neutral and sialylated glycans of CHO-expressed glycoproteins", Carbohydrate Research, vol. 347, p. 121-129, (2012).
Wheeler et al., "Derivatization of Sialic Acids for Stabilization in Matrix-assisted Laser Desorption/ionization Mass Spectrometry and Concomitant Differentiation of alpha(2→3)- and alpha(2→6)-isomers," Rapid Commun. Mass Spectrom., vol. 23, p. 303-312, (2009).
Zhang et al., "Highly a-Selective Synthesis of Sialyl Spirohydantoins by Regiospecific Domino Condensation/O→N Acyl Migration/N-Sialylation of Carbodiimides with Peracetylated Sialic Acid", J. Or. Chem., vol. 75, p. 3552-3557, (2010).

* cited by examiner

*Primary Examiner* — Layla D Berry
(74) *Attorney, Agent, or Firm* — Hoxie & Associates LLC

(57) ABSTRACT

The present invention concerns methods of derivatizing sialic acids which may be present on glycan moieties. This can be of use in determining the glycosylation profiles of, for example, glycoproteins and glycolipids and the use of such methods in clinical analysis as well as biological development and control.

25 Claims, 13 Drawing Sheets

GLYCAN ANALYSIS

CROSS-REFERENCE TO RELATED APPLICATIONS

Figure 1:
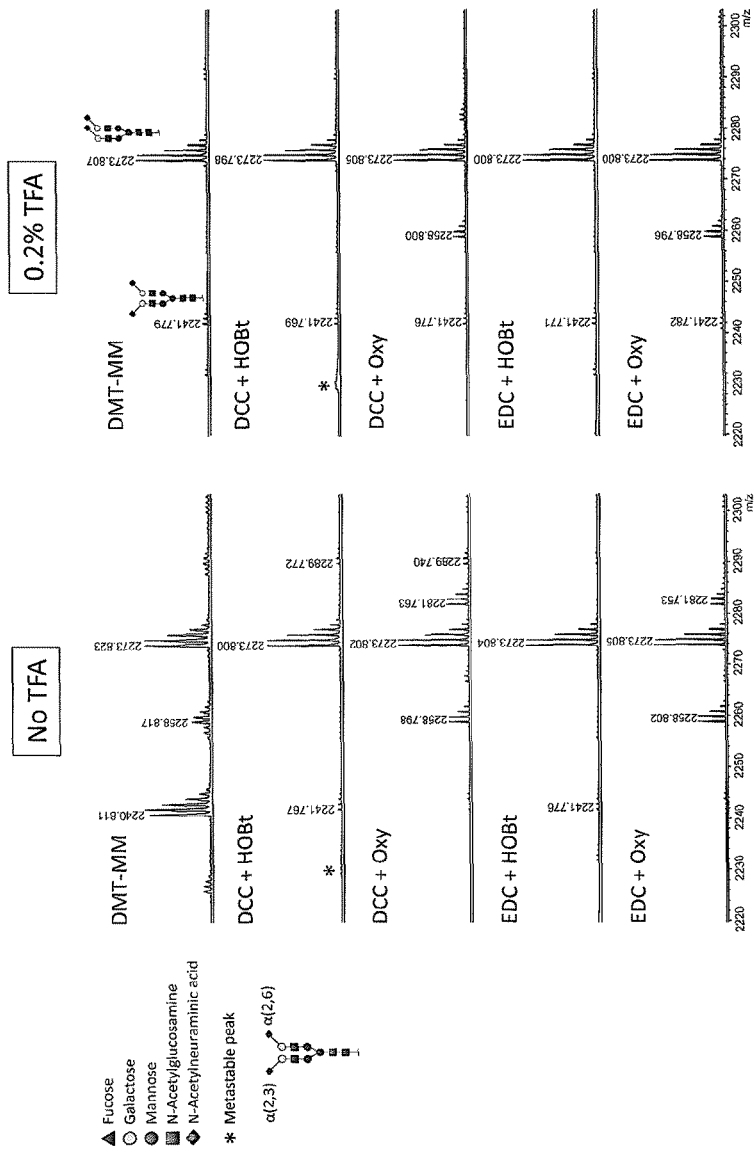

This application is a National Stage Entry of International Application No. PCT/EP2014/075189, filed on Nov. 20, 2014, which claims priority from United Kingdom Patent Application No. 1320571.1, filed on Nov. 21, 2013, the contents of each of which are hereby incorporated by reference in their entirety.

FIELD OF INVENTION

The present invention concerns methods of derivatising sialic acids which may be present on glycan moieties. This can be of use in determining the glycosylation profiles of, for example, glycoproteins and glycolipids and the use of such methods in clinical analysis as well as biological development and control.

BACKGROUND TO THE INVENTION

Glycosylation is a common post-translational modification having significant effects on protein characteristics like solubility, folding and receptor binding activity [1-3]. An increasing number of diseases have shown association with changes in glycosylation, including various forms of cancer, autoimmunity and congenital disorders [4-8]. Because of this, the profiling of glycans of individual proteins or more complex samples like plasma can serve as an important clinical biomarker [9]. In addition, glycans are known to affect the activity, stability and immunogenicity of biopharmaceuticals, requiring careful monitoring and control [10, 11].

An important characteristic of glycosylation is the presence of sialic acids (such as N-acetylneuraminic acid and N-glycolylneuraminic acid) [12]. These monosaccharides have shown many roles in cellular communication, interact with specific types of lectins, and have been associated with cancer and metastaticity [13-15]. In case of human glycosylation, sialic acids may be attached to a terminal galactose either by $\alpha2,6$ or $\alpha2,3$ glycosidic linkage, showing different functionality as a consequence. $\alpha2,3$-linked N-acetylneuraminic acids for example, are specifically required for formation of sialyl Lewis X structures, which have shown to be indicative for metastasis of several types of cancer [16-19], whereas $\alpha2,6$-linked sialic acids show roles in galectin inhibition, thereby promoting cell survival [20-22]. With an increasing need for analysis, the development of methods for high-throughput (HTP) glycomics is of great interest.

A technique well suited for glycomic studies is matrix-assisted laser desorption/ionization (MALDI) time-of-fight (TOF) mass spectrometry (MS), as it can rapidly provide information on the composition, sequence and branching of glycan structures [23]. Sialic acids, however, are attached to glycans by a relatively weak bond, often leading to loss of the residue by in-source and metastable decay during the respective ionization and acceleration phases in the mass spectrometer. In addition, sialylated glycan species tend to show high variability in salt adduction, resulting in multiple signals for single glycan compositions. Moreover, a carboxyl group such as present on a sialic acid facilitates negative ionization by MALDI considerably, generating a bias in signal intensity when comparing acidic and neutral oligosaccharides, preventing relative quantification of mixed samples [24].

One way to improve MALDI-TOF-MS measurement of sialylated glycans is by derivatisation [25, 26]. In particular, chemical modifications of the sialic acid carboxyl group can prevent metastable decay to a large degree, and the resulting reaction product can be analyzed in positive-mode MALDI-TOF-MS together with the non-sialylated species [24, 25, 27]. Interestingly, reactions conditions have been developed which allow derivatisation of sialic acids in a linkage-dependent manner, differentially derivatising $\alpha2,3$-linked sialic acids (prone to lactone formation) and $\alpha2,6$-linked sialic acids (undergoing other chemical modification such as esterification and amidation). Methods described in literature involve methyl esterification or (methyl)amidation, but these typically require highly purified glycan samples, harsh conditions or long reaction times, and do not show complete linkage-specificity [28-30]. While these procedures are informative for the analysis of sialylated oligosaccharides, suitability for HTP analysis of complex samples is limited.

It is amongst the objects of the present invention to obviate and/or mitigate at least one of the aforementioned disadvantages.

SUMMARY OF THE INVENTION

The present invention is based upon studies conducted by the present inventors to develop sialic acid derivatisation methods suitable for use with MALDI-TOF-MS measurement of sialylated glycans.

In a first aspect there provided a method for derivatising sialic residues present on glycan moieties, the method comprising:

reacting a biological sample or glycan preparation with a reagent comprising at least one carbodiimide(s) and at least one triazole or ethyl 2-cyano-2-(hydroxyimino)acetate (Oxyma pure), in order to derivatise any sialic acid residues which may be present on glycan moieties present in the biological sample.

The inventors have observed that derivatisation is by way of linkage-specific alkyl esterification and lactone formation of the sialic acid residues with little or no amidation being observed. Typically, less than 1% amidation, such as less than 0.5%, or 0.1% amidation may be observed. The inventors have observed that acetylation of sialic acids may be preserved under chosen derivatisation conditions. Furthermore, derivatisation may take place to both N-acetylneuraminic acids and N-glycolneuraminic acids, as well as to sialic acids linked to N-acetylhexosamine residues such as N-acetylglucosamine.

The present invention can enable the derivatised sialic acid residues present on the glycan moieties to be analysed by mass spectrometric techniques, such as matrix assisted laser desorption/ionization time-of-flight (MALDI-TOF) techniques known in the art, as will be further described herein. However, the derivatisation reaction may allow other types of analysis to be conducted. For example the derivatisation reaction may allow for modifying glycoconjugates and/or other glycosylated molecules in order to modify their physicochemical properties, including changing the migration positions in capillary gel electrophoresis, or release in chromatography binding assays.

Said at least one carbodiimide may be N,N'-Dicyclohexylcarbodiimde (DDC), or 1-ethyl-3-(3-dimethyl amminopropyl) carbodimiide (EDC), such as in its hydrochloride form. Said at least one carbodiimide may be provided in solution at a concentration of between 0.01-1M, such as 0.1-0.8M, typically, 0.25-0.75M.

Suitable triazoles include hydroxybenzotriazole (HOBt), typically in a hydrated from, such as the monohydrate which may also be provided in solution at a concentration of between 0.1-1M, such as 0.2-0.8M, typically, 0.25-0.75M.

The reagent may comprise a single carbodiimide and triazole/Oxyma pure combination, or mixtures comprising one or more carbodiimides in combination with one or more triazoles/oxyma pure may be provided.

Particularly preferred combinations of reagent components are DCC with HOBt, DCC with oxyma pure, EDC with HOBt and EDC with oxyma pure. A particularly preferred combination is EDC and HOBt.

Typically the reagent components are provided as a single reagent composition. The reagent components may be provided in an alcohol solution, such as methanol, ethanol, (iso)propanol or butanol. The solution of the reagent in alcohol may be 0.01-1M, such as 0.05-0.8M, 0.2-0.7 M, such as 0.4-0.6 M, especially 0.5 M. Alternatively, the reagents may be provided initially in a lyophilised form which are reconstituted with the sample and appropriate alcohol.

Typically the alcohol content for the sialic acid derivatisation reaction will be between 50% and 99%, such as 70% to 96%, especially 95% v/v.

The inventors have observed that choice of alcohol can affect the degree and type of derivatisation which occurs. In certain embodiments, the preferred alcohol in methanol or ethanol and in a particularly preferred embodiment, the alcohol is ethanol.

The reaction may preferably be carried out under acidic or neutral conditions (for example, pH 1.9 to pH 7.6). This may be achieved by addition of an acid. Such as trifluoracetic acid (TFA), such as 0.1%-0.4% TFA. The inventors have observed that acidic conditions may reduce or minimise unwanted side-products.

In fact, the present inventors have observed that the use of acidic conditions can serve to minimise side products observed the using the previously known derivatising agent 4-(4,6-dimethoxy-1,3,5-triazin-2-yl)-4-methylmorpholinium chloride (DMT-MM), particularly when using impure samples.

This is in a further aspect there is provided a method of derivatising sialic acid residues present on glycan moieties, the method comprising:

reacting a biological sample or glycan preparation with DMT-MM under acidic conditions; in order to derivatise any sialic acid residues which may be present on glycan moieties present in the biological sample.

Preferably the acidic conditions are provided by the addition of TFA to the reaction, such as 0.1%-0.4% TFA, typically 0.2% TFA.

The present invention may be carried out on purified or impure samples. For example, the present inventors have been able to derivatise sialylated glycans from plasma and fibrinogen samples which have been digested enzymatically in order to make available any glycans for reaction. A suitable enzyme for use in releasing N-linked oligosaccharides is an endoglycosidase, such as PNGase F. Advantageously the present inventors have been able to carry out derivatisation reactions of the present invention without any purification being required following the above-described enzymatic reaction, which is contrary to prior art techniques which teach that purification of glycans from a biological sample, such as plasma, is required before derivatisation can be carried out. Without wishing to be bound by theory, it appears that the alcohol solution in which the reagent is/are provided, may be capable of precipitating proteins and the like, which may otherwise interfere with the derivatisation reaction.

Thus, in a further aspect, the present invention provides a method of derivatising sialic acid residues present on glycan moieties, the method comprising:

treating a biological sample or glycan preparation, typically enzymatically treating, in order to release glycan moieties present within the sample; and directly reacting the treated biological sample with an alcohol solution comprising a reagent comprising at least one carbodiimide(s) and at least one triazole or ethyl 2-cyano-2-(hydroxyimino)acetate (Oxyma pure); or DMT-MM, in order to derivatise any sialic acid residues which may be present on glycan moieties present in the biological sample.

The term "directly" as used above is understood to mean that the sample is not subjected to a purification step prior to the derivatisation reaction being carried out. It does not refer to a period of time and hence does not mean that the derivatisation step must be carried out immediately. There can be a period of delay between the treatment step and the derivatisation step.

Optionally the reagent solution may be acidic, as described above.

In a further aspect there is proved an alcohol solution comprising at least one carbodiimide(s) and at least one triazole or ethyl 2-cyano-2-(hydroxyimino)acetate (Oxyma pure), for use in derivatising sialic acid residues present on glycan moieties.

There is also provided use of the above alcohol solution in derivatising sialic acid residues present on glycan moieties.

The preferred alcohols and concentrations, as well as the components of the solution and their concentrations, are herein defined above.

Advantageously, the present derivatisation reactions of the present invention are carried out in a single step and may therefore be considered as a "one-pot" reaction. The (one pot) derivatisation reaction may be carried out at any suitable reaction temperature for any suitable length of time. Typical reactions times are from about 1 minute to about 5 hours, such as from about 5 minutes to about 2 hours (for example from about 15 minutes to about 1 hour).

Typical reaction temperatures are from about 0° C. to about 100° C., such as from about 10° C. to about 80° C. (for example from about 30° C. to about 60° C.).

The invention may be carried out on any glycan preparation containing, for example glycoprotein, glycolipid, glycoconjugates and other glycosylated molecules. Typically, the glycans may be released from glycan containing molecules contained within a biological sample of interest, or may remain attached to the moiety or portion thereof, such as a peptide or lipid moiety, for example. In either case, such preparations are referred to as a glycan preparation. Examples of glycoproteins include hormones, such as erythropoietin.

The term "glycan preparation" as used herein refers to a set of glycans obtained according to a particular production method. In some embodiments, glycan preparation refers to a set of glycans obtained from a glycoprotein preparation.

The term "biological sample", as used herein, refers to any solid or fluid sample obtained from, excreted by or secreted by any living cell or organism, including, but not limited to, tissue culture, bioreactors, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture. The biological sample may be used directly, or may have been subjected to one or more purification or reaction steps in order to isolate and/or enhance the presence of particular glycoproteins, glycolipids, glycoconjugates and the like.

The glycoprotein may be a cell-surface glycoprotein. As used herein, the term "cell-surface glycoprotein" refers to a glycoprotein, at least a portion of which is present on the exterior surface of a cell. In some embodiments, a cell-surface glycoprotein is a protein that is positioned on the cell surface such that at least one of the glycan structures is present on the exterior surface of the cell. In many embodiments of the disclosure, a cell-surface glycan is covalently linked to a polypeptide as part of a cell-surface glycoprotein. A cell-surface glycan can also be linked to a cell membrane lipid, and is termed a glycolipid.

The term "glycolipid" as used herein refers to a lipid that contains one or more covalently linked sugar moieties (i.e., glycans).

The sugar moiety(ies) may be in the form of monosaccharides, disaccharides, oligosaccharides, and/or polysaccharides. The sugar moiety(ies) may comprise a single unbranched chain of sugar residues or may be comprised of one or more branched chains. In certain embodiments of the disclosure, sugar moieties may include sulfate and/or phosphate groups. In certain embodiments, glycoproteins contain O-linked sugar moieties; in certain embodiments glycoproteins contain N-linked sugar moieties is understood by those skilled in the art, the peptide backbone typically comprises a linear chain of amino acid residues. In certain embodiments, the peptide backbone spans the cell membrane, such that it comprises a transmembrane portion and an extracellular portion. In certain embodiments, a peptide backbone of a glycoprotein that spans the cell membrane comprises an intracellular portion, a transmembrane portion, and an extracellular portion. In certain embodiments, methods of the present disclosure comprise cleaving a cell surface glycoprotein with a protease to liberate the extracellular portion of the glycoprotein, or a portion thereof, wherein such exposure does not substantially rupture the cell membrane. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments of the disclosure, sugar moieties may include sulfate and/or phosphate groups. Alternatively, or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties. In certain embodiments, methods disclosed herein comprise a step of analyzing any or all of cell surface glycoproteins, liberated fragments (e.g., glycopeptides) of cell surface glycoproteins, cell surface glycans attached to cell surface glycoproteins, peptide backbones of cell surface glycoproteins, fragments of such glycoproteins, glycans and/or peptide backbones, and combinations thereof.

The term "glycoconjugate", as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, glycolipids, proteoglycans, etc The present invention is concerned with linkage-specific sialic acid stabilisation of glycans and their analysis. The term "sialic acid", as used herein, is a generic term for the N- or O-substituted derivatives of neuraminic acid, a nine-carbon monosaccharide. The amino group of neuraminic acid typically bears either an acetyl or a glycolyl group in a sialic acid. The hydroxyl substituents present on the sialic acid may be modified by acetylation, methylation, sulfation, and phosphorylation. The predominant sialic acid is N-acetylneuraminic acid (Neu5Ac). Sialic acids impart a negative charge to glycans, because the carboxyl group tends to dissociate a proton at physiological pH. Exemplary deprotonated sialic acids are as follows:

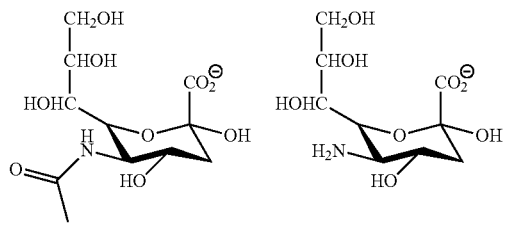

N-acetylneuraminic acid (Neu5Ac; left) and Neuraminic acid (Neu; right)

Methods of the present disclosure can be utilized to analyze glycans in any of a variety of states including, for instance, free glycans, glycoconjugates (e.g., glycopeptides, glycolipids, proteoglycans, etc.), or cells or cell components, etc.

It may also be desirable to label the glycan moieties, present in the biological sample or glycan preparation using techniques known to the skilled addressee. For example, the reducing end of a sugar moiety may easily be labelled, such as with a radio or non-radioactive label isotope, or fluorescent or luminescent label. For example, such labeling agents may be used to label the glycan via reaction of the amine function group of the labeling agent with the N-glycan's reducing (—CHO) end by reductive amination. One of ordinary skill in the art will appreciate that a wide variety of reaction conditions may be employed to promote this reductive amination reaction, therefore, a wide variety of reaction conditions are envisioned; see generally, March's Advanced Organic Chemistry: Reactions, Mechanisms, and Structure, M. B. Smith and J. March, $5^{th}$ Edition, John Wiley & Sons, 2001, and Comprehensive Organic Transformations, R. C. Larock, $2^{nd}$ Edition, John Wiley & Sons, 1999. Suitable reductive amination conditions include providing a reducing agent, such as $NaCNBH_3$, 2-picoline borane or $NaBH(OAc)_3$, and maintaining an acidic to slightly acidic pH of the reaction mixture. It is expected that such labeling, if required, will take place prior to the sialic acid derivatisation, but could also take place after the derivatisation reaction.

The derivatised and optionally labelled sialylated glycans may desirably be purified following derivatisation and/or labelling. Any suitable purification technique may be used. In one embodiment of the invention, the derivatised and optionally labelled sialylated glycans can be purified by hydrophilic interaction chromatography (HILIC), porous graphitized carbon solid phase extraction (PGC-SPE), cationic exchange resins, liquid-liquid extraction or a mixture of the foregoing.

In one preferred embodiment, the at least one derivatised and optionally labelled glycans may be purified by HILIC. This may be carried out using cotton wool or other forms of cotton. In summary, the at least one derivatised and optionally labelled sialylated glycans are applied to a stationary phase comprising cotton; the stationary phase is washed with a first solvent; and the at least one derivatised and optionally labelled sialylated glycans are eluted from the stationary phase with a second solvent. Typically the sample comprising said at least one derivatised and optionally labelled sialylated glycan is mixed with an organic solvent; wherein the organic solvent comprises acetonitrile, methanol, ethanol, propanol, isopropanol, butanol, or tetrahydrofuran.

Preferably, the organic solvent is between 25% and 80% v/v acetonitrile in alcohol; more preferably wherein the organic solvent is between 40% to 60% v/v acetonitrile in alcohol; more preferably wherein the organic solvent is 50% v/v acetonitrile in alcohol Preferably, the sample comprises a 1:1 mixture with the organic solvent.

The first solvent for washing is a solvent mixture comprising water, an organic solvent and an acid. More preferably, the organic solvent is acetonitrile, methanol, ethanol, propanol, isopropanol, butanol or tetrahydrofuran and the acid is trifluoroacetic acid (TFA), formic acid, acetic acid, pentafluoropropionic acid, or heptafluorobutyric acid. Conveniently, the above first solvent mixture comprises between 70% and 95% v/v organic solvent and between 0.1% and 3% v/v acid in water. Preferably, the solvent mixture comprises between 80% and 90% v/v organic solvent and between 0.5% and 2% v/v acid in water. Preferably, the solvent mixture comprises 85% v/v organic solvent, typically acetonitrile and 1% v/v acid, typically TFA in water.

Preferably, the second solvent comprises a polar solvent. More preferably, the polar solvent is water, dimethylsulfoxide, or dimethylformamide. Optionally, the second solvent comprises a more polar solvent than the first solvent.

Without wishing to be bound by theory, it is expected that the washing removes salts, non-glycosylated peptides, lipids, detergents, excess reducing-end label, reducing agents, sialic acid activator reagents, denaturants, denatured proteins and the like from the stationary phase.

Preferably, the stationary phase is held in an open ended vessel. The vessel may be open at one end, or at both ends. Preferably the vessel is open at both ends.

Optionally, the open-ended vessel is a pipette, a multichannel pipette or a pipette tip. Alternatively, the open-ended vessel may be the well of a multi-well plate, such as a 96 or 384 well plate.

Conveniently, the purification step can be used to extract said one or more derivatised and optionally labelled glycans in order to render them sufficiently pure for further analysis, such as MALDI-TOF-MS.

The derivatised sialic residues are found to be stable and the reaction solutions, before or after further purification may be stored for a period of time (for example 1 day to a few weeks) at 4° C. to 10° C. prior to any further analysis being carried out. The reacted, optionally purified samples may also be dried, with subsequent analysis being conducted on reconstituted samples.

Further analysis by mass spectroscopy techniques, especially MALDI-TOF analysis is a particularly feature aspect of the present invention. Thus, in accordance with the present invention, in a preferred embodiment, the above described methods of the present invention further comprise subjecting the derivatised and optionally labelled sialylated glycans to detection by mass spectrometric analysis, particularly MALDI-TOF analysis, liquid chromatography, gas chromatography, capillary electrophoresis, anion-exchange chromatography or a mixture of the foregoing The present inventors have observed that analysis may be facilitated by the addition of Na+, such as in the form of NaOH, prior to subjecting the derivatised sample to MALDI-TOF analysis. Typically, 0.1-10 mM, such as 0.5-5 mM, especially 1 mM Na+ carrier, such as NaOH, may be added to a matrix material (0.1-20 mg/ml matrix concentration, such as 1-10 mg/ml, typically 5 mg/ml) to which the derivatised sample is added.

The inventors have also observed that impurities, variations in salt adduction, and variations in matrix crystallization which may interfere with the MALDI-TOF analysis may be removed by carrying out a recrystallisation step on the derivatised sample prior to the sample being analysed by MALDI-TOF. For example, a sample of the purified derivatised sample which is to be analysed may be allowed to dry and a recrystallisation reagent, such as ethanol containing up to 5% water added to the dried sample in order to allow recrystallisation and further purification of the sample to be analysed. For example, the initial crystal may be formed by mixing the sample with a matrix solution and allowing the mixture to dry). The matrix solution for example being 2,5-dihydroxybenzoic acid (2,5-DHB) in 50% acetonitrile (ACN), a mixture of matrix substances such as 9:1 2,5-DHB and 2-methoxy-5-hydroxybenzoic acid, or other (microcrystalline) matrices such as 6-aza-2-thiothymine (ATT), 3-aminoquiniline (3AQ), 2,4,6-trihydroxyacetophenone (THAP), 2-(4-hydroxyphenylazo)benzoic acid (HABA) or α-cyano-4-hydroxycinnamic acid (CHCA).

It will be appreciated from the foregoing that the present invention may be carried out in a manual, semi-automated or fully automated fashion The methods of the present disclosure may be used to significantly expedite one or more stages of process development for the production of a therapeutic or other commercially relevant glycoprotein of interest. Non-limiting examples of such process development stages that can be improved using methods of the present disclosure include cell selection, clonal selection, media optimization, culture conditions, process conditions, and/or purification procedure. Those of ordinary skill in the art will be aware of other process development stages that can be improved.

Representative therapeutic glycoprotein products whose production and/or quality can be monitored in accordance with the present disclosure include, for example, any of a variety of hematologic agents (including, for instance, immunoglobulins, erythropoietins, blood-clotting factors, etc.), interferons, colony stimulating factors, antibodies, enzymes, and hormones.

The methods can also be utilized to monitor the extent and/or type of glycosylation occurring in a particular cell culture, thereby allowing adjustment or possibly termination of the culture in order, for example, to achieve a particular desired glycosylation pattern or to avoid development of a particular undesired glycosylation pattern. The methods can also be utilized to assess glycosylation characteristics of cells for example, even before the cells or cell lines have been engineered to produce the glycoprotein, or to produce the glycoprotein at a commercially relevant level.

In some embodiments of the disclosure, a desired glycosylation pattern for a particular target glycoprotein is known, and the technology described herein allows the monitoring of culture samples to assess progress of the production along a route known to produce the desired glycosylation pattern. For example, where the target glycoprotein is a therapeutic glycoprotein, for example having undergone regulatory review in one or more countries, it will often be desirable to monitor cultures to assess the likelihood that they will generate a product with a glycosylation pattern as close to identical with the established glycosylation pattern of the pharmaceutical product as possible, whether or not it is being produced by exactly the same route. As used herein, "close to identical" refers to a glycosylation pattern having at least 90%, 95%, 98% or 99% correlation to the established glycosylation pattern of the pharmaceutical product. In such embodiments, samples of the production culture are typically taken at multiple time points and are compared with an established standard or with a control culture in order to assess relative glycosylation.

To improve the accessibility of the glycosylation site to the enzyme, most glycoproteins require a protein denaturation step. Typically, this is accomplished by using detergents and disulfide-reducing agents, although methods of denaturing a glycoprotein for use in accordance with the present disclosure are not limited to the use of such agents. For example, exposure to high temperature can be sufficient to denature a glycoprotein such that a suitable enzyme for cleaving glycan structures is able to access the cleavage site. In certain embodiments, a combination of detergents, disulfide-reducing agents, high temperature, and/or other agents or reaction conditions is employed to denature a glycoprotein It is noted that also capable of removing glycans in dilute ammonium hydroxide solution. Thus, use of PNGase F to cleave glycans from glycoproteins has the advantage that the dilute ammonium hydroxide may additionally aid in solubility and some unfolding of the protein substrates. Additionally. N-linked glycans may be cleaved from a glycoprotein using chemical methods. For example, an N-linked glycan may be released via treatment with hydrazine to provide a hydrazide of the N-glycan (i.e., hydrazinolysis).

DETAILED DESCRIPTION

The present invention will now be further described with reference to the figures which show.

FIG. 1 shows a reflectron-positive mode (RP) MALDI-TOF-MS spectrum after methyl esterification of PNGase F-released plasma N-glycome. The samples were reacted using a variety of activator/reagent combinations and acidic conditions in methanol. Shown here is the most abundant disialylated N-glycan present in such a spectrum. The mass of 2273.804 Da corresponds to a fully methyl esterified reaction product [M+Na]$^+$, whereas masses of 2281.770 Da and 2289.736 Da correspond to species lacking one or two methyl groups with resulting sodium salt formation ([M-H+2Na]$^+$ and [M-2H+3Na]$^+$). Reaction products at 2258.804 Da indicate carbonyl amidation, whereas 2241.777 Da indicates a lactonised reaction product. EDC+HOBt was selected as most promising on basis of modification completeness and lack of side reactions, without the need for acid. Symbols are used throughout the document to indicate the monosaccharide residues fucose (triangle), galactose (light circle), mannose (dark circle), N-acetylglucosamine (square) and N-acetylneuraminic acid (diamond), whereas metastable peaks are indicated by an asterisk. In case of known sialic acid linkages, α2,3 is indicated by a left angle, and α2,6 by a right angle. Linkages of other residues were not evaluated, and compositions as well as structural schemes shown are based on literature [35, 37, 38].

Figure 2:
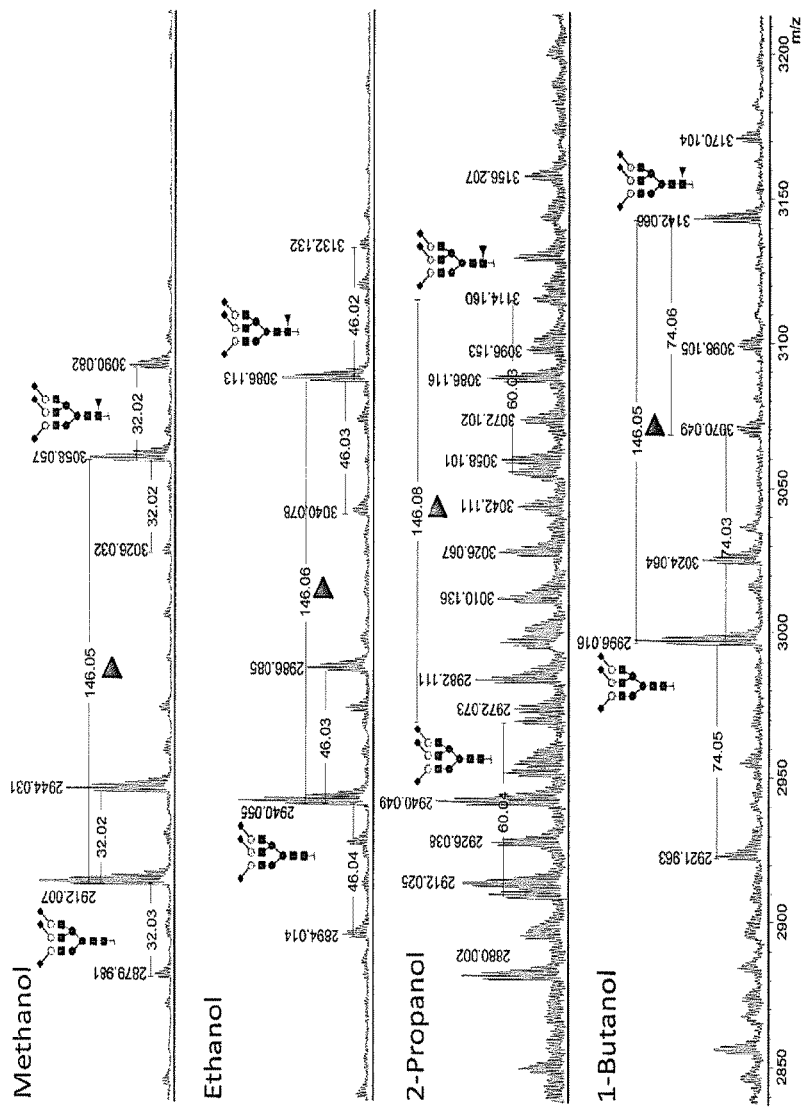

FIG. 2 shows RP MALDI-TOF-MS spectra after plasma N-glycome ethyl esterification with EDC+HOBt using methanol, ethanol, isopropanol and n-butanol as solvents and alkyl donor. Shown here are trisialylated compositions with various sialic acid linkage types. Glycan species show lactonisation, and esterification by methanol (32.026 Da), ethanol (46.042 Da), propanol (60.058 Da) and butanol (74.073 Da). All alcohols show to be an alkyl group donor for linkage-specific sialic acid derivatisation, while methanol and ethanol show the highest unoptimised reaction efficiency. Relative ratios of the lactonised and alkyl esterified signals however, differ per alcohol.

Figure 3:
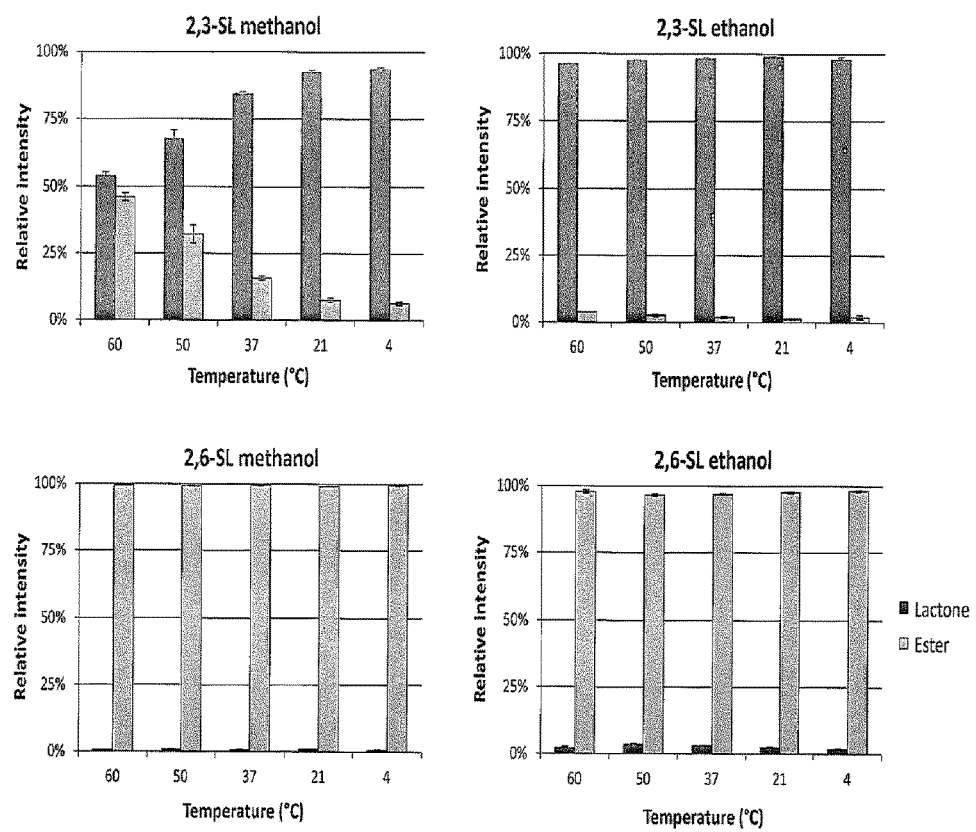

FIG. 3 shows a triplicate analysis of oligosaccharide standards with specified sialic acid linkage (sialyllactose with either a α2,3- or α2,6-linked sialic acid) after EDC+HOBt alkylation in either methanol or ethanol at varying temperatures. Shown in the graph are the average relative intensities of the lactonised and esterified reaction products, with the error bars indicating standard deviation. 2,6-linked sialic acids show to preferably form an ester with both methanol and ethanol at all temperatures. Reacting 2,3-linked sialic acids in methanol however, shows a temperature dependent effect, at best 93.6% (SD±0.9%) of the desired lactonised product being formed at 4° C. Using ethanol as alkyl donor on the other hand, shows on average 97.7% (SD±0.9%) lactonisation across all temperatures, and is therefore most suitable for separating α2,3- and α2,6-linked sialic acids.

Figure 4:
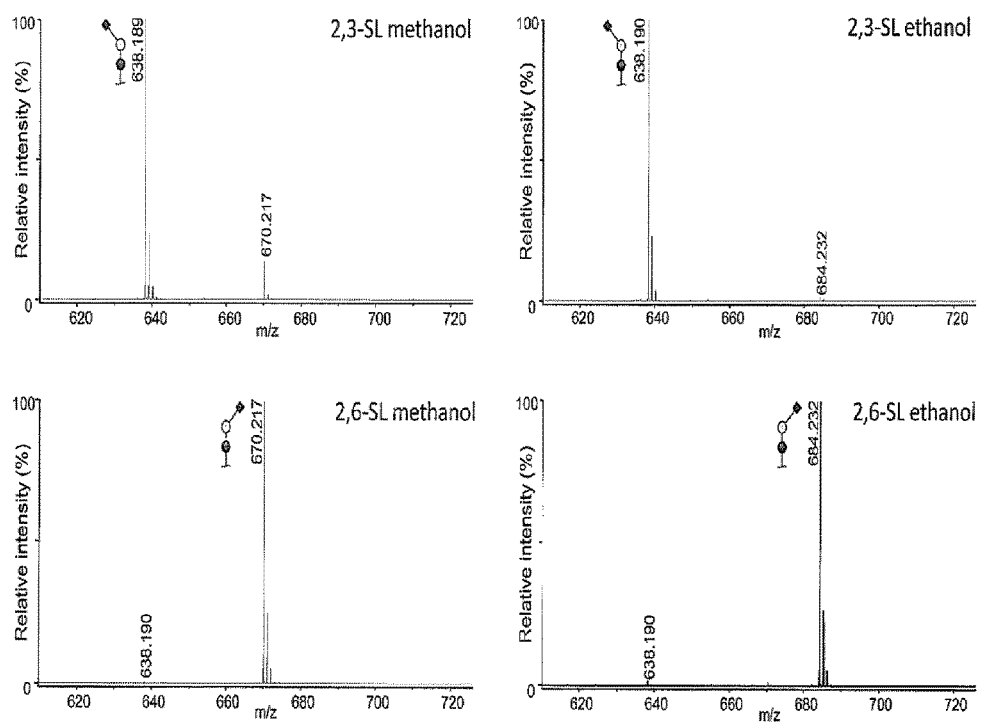

FIG. 4 shows RP MALDI-TOF-MS spectra of 3'- and 6'-sialyllactose when alkyl esterified 1 h at 37° C. with EDC+HOBt in methanol or ethanol. Lactonised reaction product is visible at 638.190 Da [M+Na]+, with the esterified masses being 670.217 and 684.232 Da in case of methanol and ethanol respectively. In no cases the mass of 678.183 Da was visible, which would be indicative for underalkylation. Reaction in ethanol shows the highest specificity for sialic acid linkage with undesired reaction products only appearing in minimal amounts.

Figure 5:
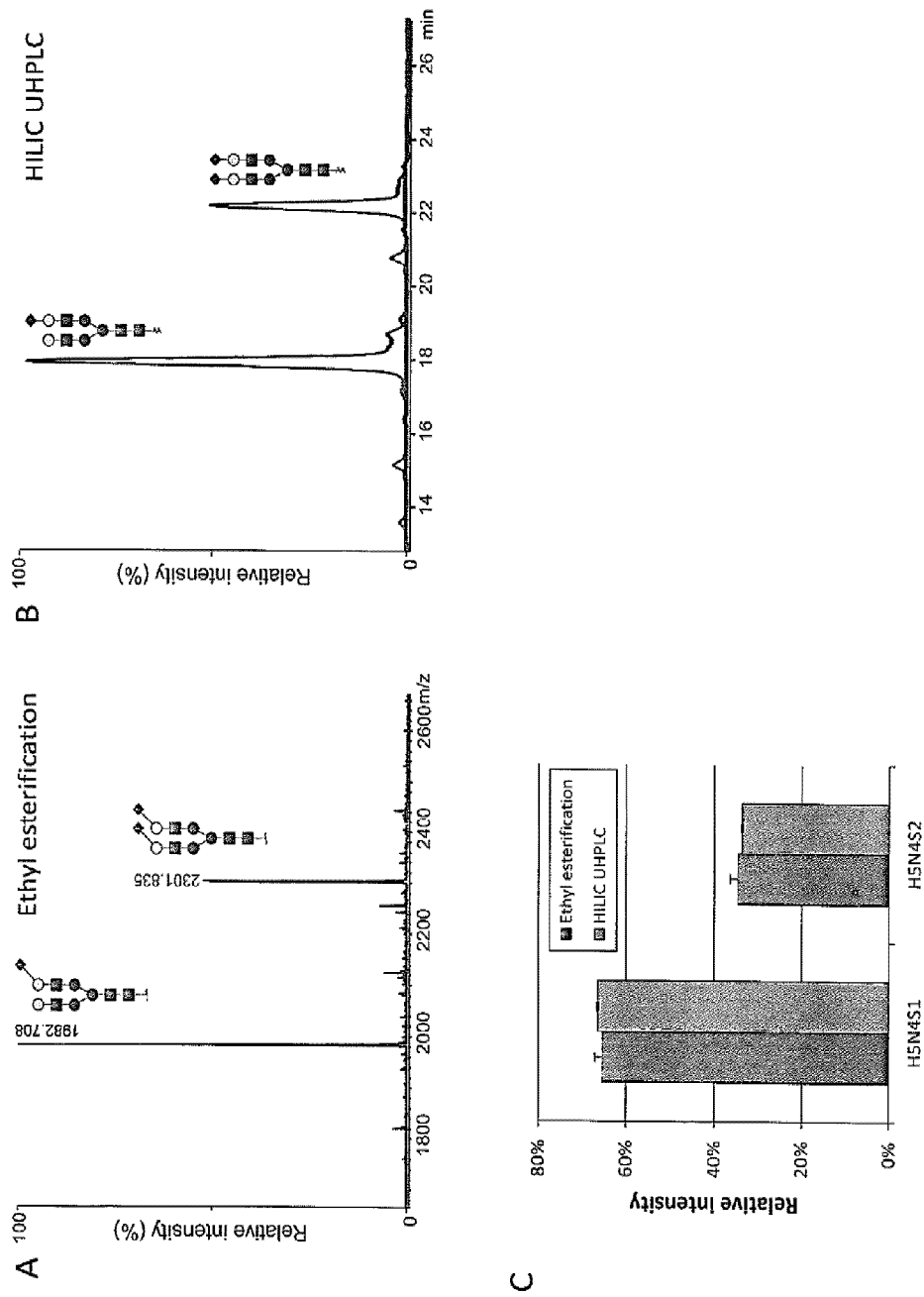

FIG. 5 shows released fibrinogen N-glycans as studied by A) RP MALDI-TOF-MS after 1 h 37° C. EDC+HOBt ethyl esterification, and B) 2-AA labeling and HILIC UHPLC with fluorescent detection. C) Triplicate analysis and relative quantification of the mono- and disialylated structures shows highly comparable relative signal intensities between MALDI-TOF-MS and UHPLC analysis. Abbreviations used are: hexose (H), N-acetylhexosamine (N), fucose (F), and N-acetylneuraminic acid with either unspecified linkage (S), α2,3-linkage as indicated by lactonisation (L), or α2,6-linkage as indicated by esterification (E). The accompanying number indicates the number of residues. Error bars show standard deviation.

Figure 6:
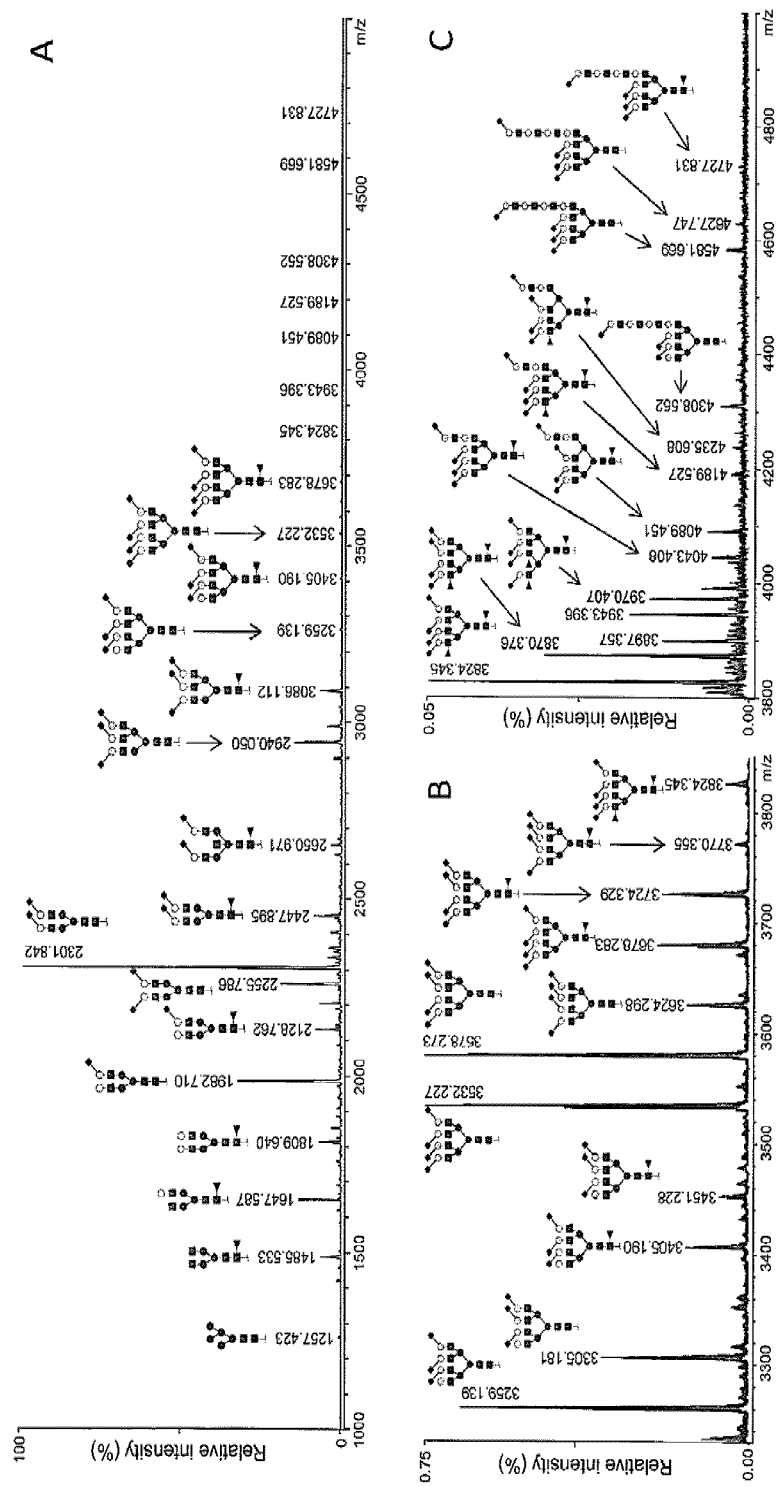

FIG. 6 shows a RP MALDI-TOF-MS spectrum after applying the 1 h 37° C. EDC+HOBt ethyl esterification protocol for plasma N-glycome analysis. A) Complete spectrum overview showing relative intensities from 1000 Da to 5000 Da. B) Intermediate range spectrum from 3200 Da to 3800 Da. C) High range spectrum from 3800 Da to 5000 Da showing glycan derivable masses up to 4727.640 Da. While the mass precision makes most compositional assignments likely, the structures shown are based on literature and may not reflect the actual sample.

FIG. 7 shows a reproducibility assay of 1 h 37° C. EDC+HOBt ethyl esterification. 24 samples originating from a common stock of plasma were independently released by PNGase F, ethyl esterified, purified by HILIC SPE, crystallized with matrix, recrystallized with ethanol, and analysed by RP MALDI-TOF-MS. The experiment was performed three times on separate days, indicated as experiment 1-3. The graph shows the average relative intensities observed (normalized to the sum of intensities), with error bars for standard deviation. A) Relative profile of the 20 most abundant N-glycans in human plasma as observed after ethyl esterification. B) Relative profile of the range of N-glycans observable after ethyl esterification.

Figure 8:
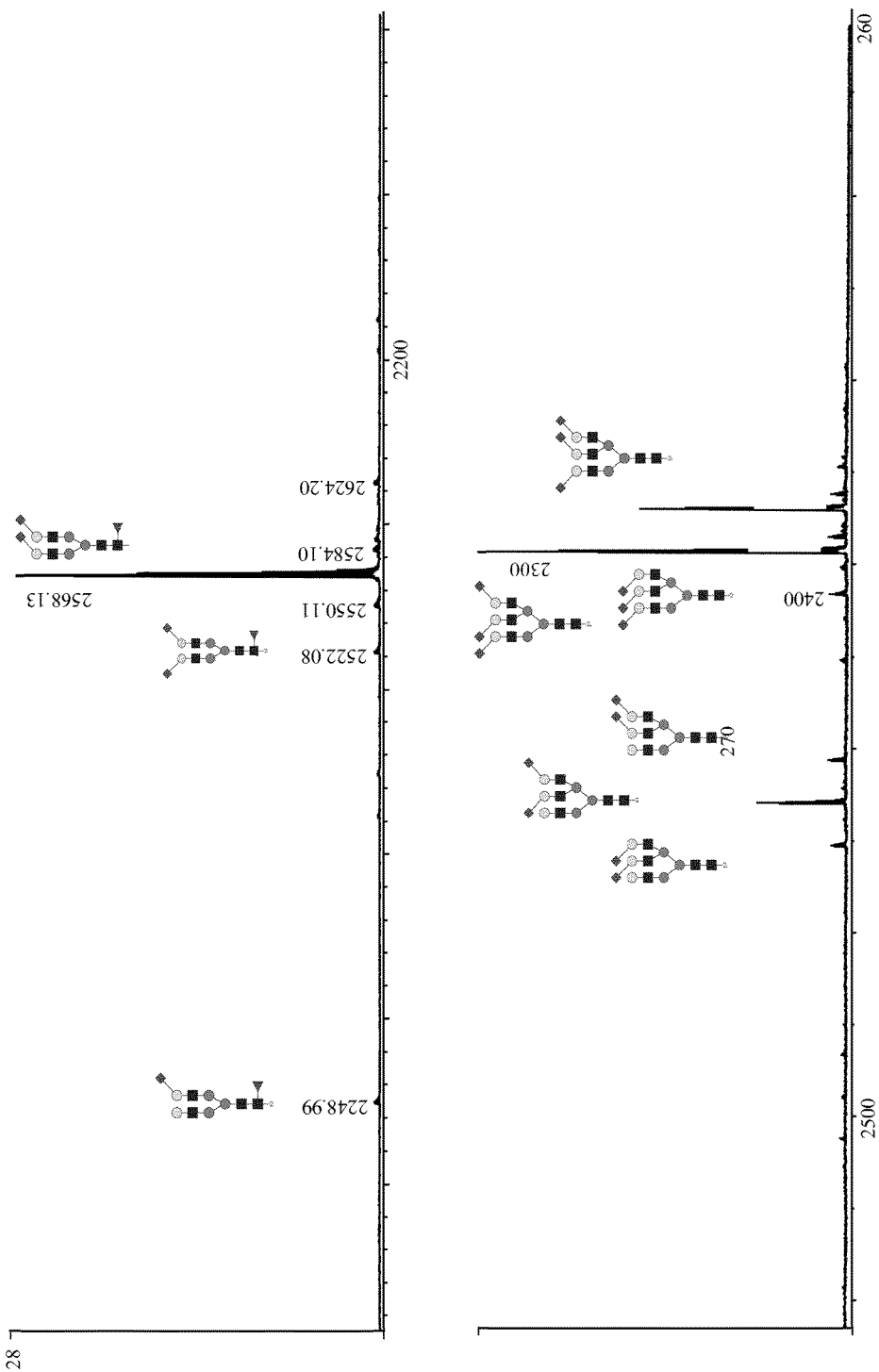

FIG. 8 shows RP MALDI-TOF-MS spectra after applying the 1 h 37° C. EDC+HOBt ethyl esterification protocol on A) 2-AB labelled A2F glycan standard (biantennary fucosylated N-glycans) and B) 2-AB labelled A3 glycan standard (triantennary N-glycans with both α2,3- and α2,6-linked sialic acids).

Figure 9:
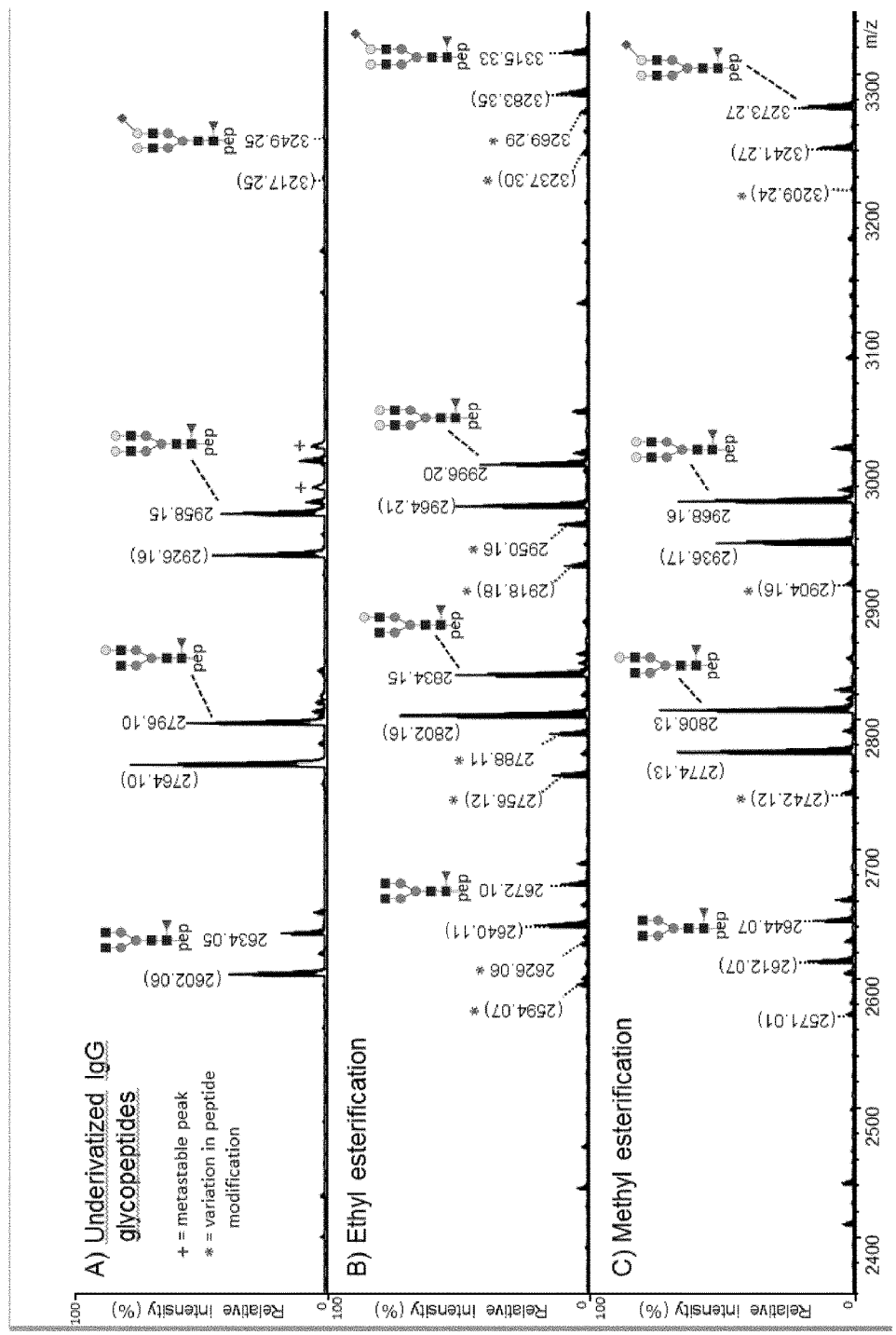

FIG. 9 shows RP MALDI-TOF-MS spectra of IgG tryptic glycopeptides A) without derivatisation, B) after 1 h incubation at 37° C. with EDC+HOBt in ethanol, and C) after 1 h incubation at 4° C. with EDC+HOBt in methanol. IgG2/3 signals (peptide sequence=EEQFNSTFR) are displayed in parentheses, IgG1 signals (peptide sequence=EEQYNSTYR) without parentheses, while IgG4 signals (peptide sequence=EEQFNSTYR) have not been indicated due to their low relative intensity. Sialylated glycopeptides show only a small signal when analyzed natively, with the metastable peaks (indicated by a plus) indicating the instability and loss of sialic acids. For both the ethanol and methanol conditions, these metastable peaks are no longer observed, and the sialylated species can be observed together with the non-sialylated variants. Signals for the esterification conditions B and C arise from one lactonisation and two esterifications on the peptide (+38.05 Da for the ethyl esterification, and +10.02 Da for the methyl esterification), with one additional esterification in per α2,6-linked sialic acid (+28.03 and +14.02 Da respectively). A side product can be seen for both the ethyl esterification and methyl esterification conditions, where one esterification has been replaced by a lactonisation (−46.04 Da and −32.03 Da respectively; indicated by an asterisk), which is minor for the methyl esterification condition.

Figure 10:
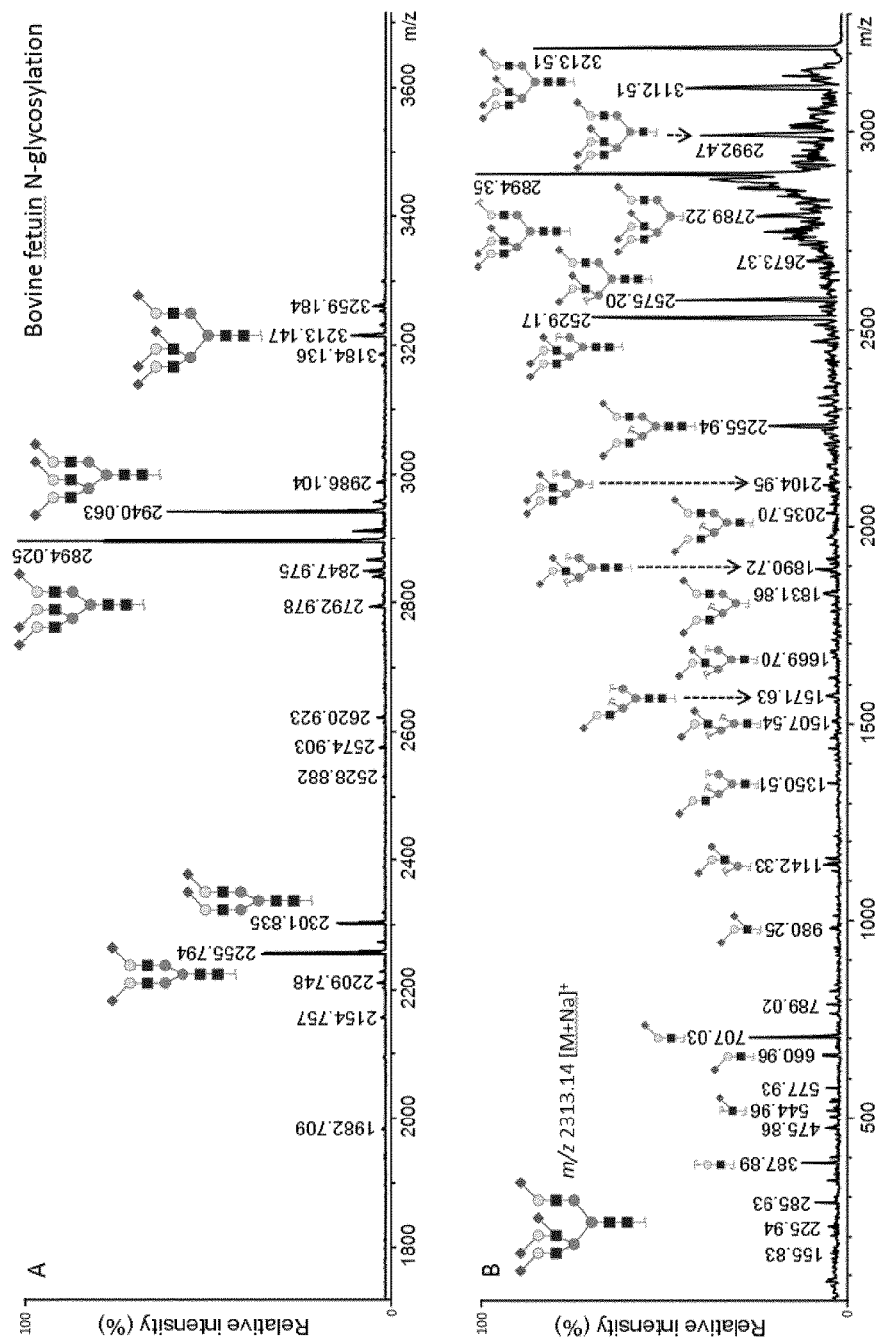

FIG. 10 shows RP MALDI-TOF-MS spectra of A) bovine fetuin N-glycosylation after ethyl esterification, and B) the fragmentation of the glycan species at m/z 3213.147 [M+Na]+, which revealed the presence of an ethyl esterified N-acetylneuraminic acid at one of the antennary N-acetylglucosamines.

Figure 11:
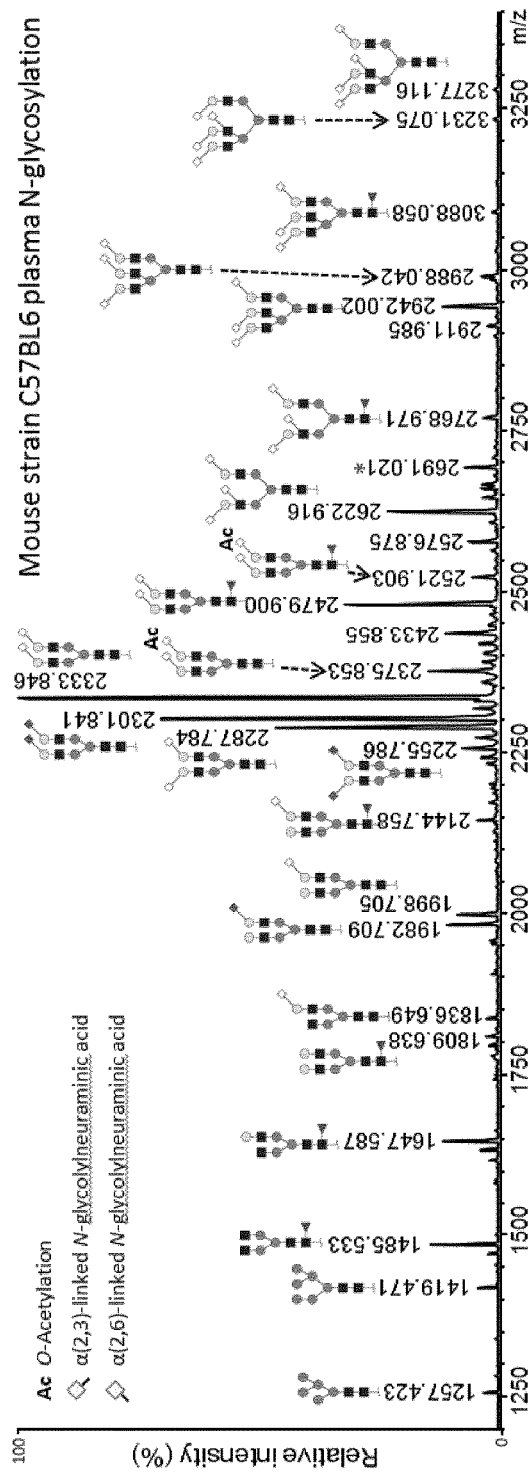

FIG. 11 shows a RP MALDI-TOF-MS spectrum of mouse strain C57BL6 plasma N-glycosylation after ethyl esterification. Next to ethyl esterified and lactonised N-acetylneuraminic acid residues, the observed signals indicate the presence and derivatisation of α2,3- and α2,6-linked N-glycolylneuraminic acids. Whereas unmodified N-glycolylneuraminic acids have an increment mass of 307.09 Da (not detected), lactonised and ethyl esterified variants have increment masses of 289.08 Da and 335.12 Da respectively. In addition, the presence of O-acetylated glycans could be observed (m/z 2375.85 and m/z 2521.90). The asterisk indicates a non-glycan signal.

Figure 12:
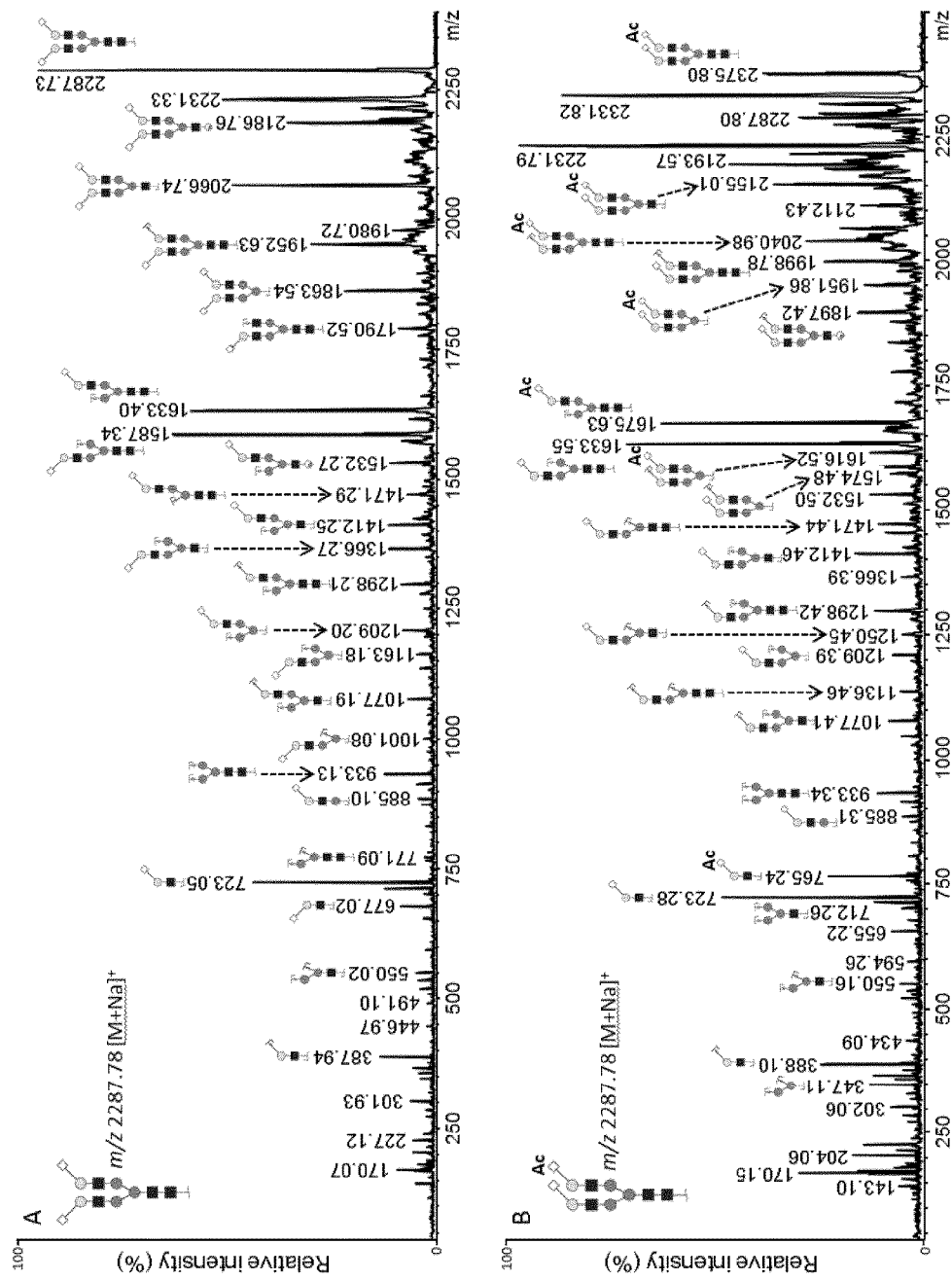

FIG. 12 shows RP MALDI-TOF/TOF-MS/MS profiles of two glycan signals from mouse strain CD57BL6 plasma after ethyl esterification. A) Shows the fragmentation of a biantennary structure containing both an ethyl esterified (α2,6-linked) and a lactonised (α2,3-linked) N-glycolylneuraminic acid. B) Shows the fragmentation of a biantennary structure with two ethyl esterified N-glycolylneuraminic acids, one of which O-acetylated.

EXPERIMENTAL SECTION

Samples

Plasma pooled from twenty human donors (Visucon-F Frozen Normal Control Plasma, citrated and 0.02M HEPES buffered) was obtained from Affinity Biologicals (Ancaster, Canada). 3'-Sialyllactose (Neu5Ac(α2,3)Gal(β1,4)Glc) sodium salt and 6'-sialyllactose (Neu5Ac(α2,6)Gal(β1,4)Glc) sodium salt (both with purities higher than 98%) were purchased from Carbosynth (Compton, UK). Both 3'- and 6'-sialyllactose were dissolved to a concentration of 100 mg/mL in Milli-Q water. Fibrinogen from human plasma was acquired from Sigma-Aldrich (Steinheim, Germany), and was incubated for 4.5 h at 37° C. in 1×PBS, resulting in a fibrinogen solution of 24.12 mg/mL.

Chemicals, Reagents and Enzymes

Milli-Q water (MQ) used in this study was generated from a Millipore Q-Gard 2 system, maintained at ≥18 MΩ. Methanol, ethanol, 2-propanol, 1-butanol, trifluoroacetic acid (TFA), glacial acetic acid, sodium dodecyl sulphate (SDS), disodium hydrogen phosphate dihydrate (Na2HPO4.2H2O), potassium dihydrogen phosphate (KH2PO4) and sodium chloride (NaCl) were purchased from Merck (Darmstadt, Germany). N,N'-Dicyclohexylcarbodiimide (DCC), hydroxybenzotriazole (HOBt) hydrate, 2-aminobenzoic acid (2-AA), 2-picoline borane (2-PB), dimethyl sulfoxide (DMSO), 50% sodium hydroxide (NaOH), 98% formic acid (FA), 25% ammonium hydroxide in water (NH4OH) and Nonidet P-40 (NP-40) were obtained from Sigma-Aldrich Chemie (Steinheim, Germany), while 1-ethyl-3-(3-dimethylaminopropyl)carbodiimide (EDC) hydrochloride and ethyl-2-cyano-2(hydroxyimino)acetate (trade name Oxyma Pure) originated from Fluorochem (Hadfield, UK). Additional components used for this study included recombinant peptide-N-glycosidase F (PNGase F) from Roche Diagnostics (Mannheim, Germany), 4-(4,6-dimethoxy-1,3,5-triazin-2-yl)-4-methylmorpholinium chloride (DMT-MM) from Santa Cruz Biotechnology (Santa Cruz, US), 2,5-dihydroxybenzoic acid (2,5-DHB) from Bruker Daltonik (Bremen, Germany) and HPLC SupraGradient acetonitrile (ACN) from Biosolve (Valkenswaard, Netherlands).

N-Glycan Release

N-glycans were released from the human plasma and fibrinogen samples as described previously[31]. 10 μL of sample was denatured by adding 20 μL 2% SDS and incubating for 10 minutes at 60° C. The release step was subsequently performed by adding 20 μl release mixture containing 2% NP-40 and 0.5 mU PNGase F in 2.5×PBS (1×PBS prepared as MQ containing 5.7 g/L Na2HPO4.2H2O, 0.5 g/L KH2PO4 and 8.5 g/L NaCl), and incubating overnight at 37° C.

Activator/Reagent Comparison

A variety of reagents and their combinations were tested for suitability with sialic acid methyl-esterification of unpurified PNGase F-released plasma N-glycome samples. DMT-MM, HOBt, Oxyma Pure, DCC and EDC were dissolved at 0.5 M in methanol, with and without 0.2% TFA. 1 μL released plasma N-glycome (approximating 14 μg of plasma protein and the glycosylation thereof) was added to 20 μL of each reagent. In addition, 1 μL released plasma N-glycome was added to 20 μL of methanol, containing reagent combinations DCC with HOBt, DCC with Oxyma Pure, EDC with HOBt or EDC with Oxyma Pure, each component at a concentration of 0.25 M, and each condition with and without 0.2% TFA. All samples were incubated 1 h at 60° C.

The reaction mixes were found not to be directly compatible with MALDI-TOF-MS, as a 1 µL spot on a Bruker Anchorchip target plate did not fully dry, both without and with matrix, and measurement of samples prepared in this way did not yield discernible analyte signals. The samples were also unresponsive to coevaporation with volatile organics (ACN, ethanol, acetone) or application of vacuum pressure. Because of this, a sample clean-up was deemed necessary for enrichment and purification of the glycans from the reaction mixture, and we chose for HILIC SPE using cotton as stationary phase, as described previously [32].

Glycans exhibited insufficient retention on the cotton stationary phase when extracting directly from the reaction mixture, yielding a very low mass spectrometric signal upon analysis. Therefore, 20 µL ACN was added and the samples incubated 15 min at −20° C. before proceeding with glycan enrichment and analysis by MALDI-TOF-MS.

Alcohol Comparison 0.25 M EDC with 0.25 M HOBt was selected as the most promising reagent combination for sialic acid esterification, and additional alcohols besides methanol were tested for use as combined solvent and alkyl donor. 0.25 M EDC 0.25 M HOBt was dissolved in methanol, ethanol, 2-propanol and 1-butanol, respectively. 1 µL of PNGase F-released plasma N-glycome was added to 20 µL of each condition, and the samples were incubated for 1 h at 60° C. After this, 20 µL of ACN was added and the samples were incubated at −20° C. before glycan enrichment and analysis by MALDI-TOF-MS.

Linkage Specificity on α2,3- and α2,6-sialyllactose

The linkage-specificity of the 0.25 M EDC 0.25 M HOBt methanol and ethanol conditions was tested using oligosaccharide standards with a known sialic acid linkage position. 1 µL 100 mg/mL (100 µg) α2,3- or α2,6-sialyllactose was added to 20 µL methanol or ethanol containing 0.25 M EDC 0.25 M HOBt. Samples were incubated 1 h at 60° C., 50° C., 37° C., 21° C. or 4° C. Hereafter, 20 µL ACN was added and all samples were incubated 15 min at −20° C. before proceeding with glycan enrichment and analysis by MALDI-TOF-MS.

Fibrinogen Glycan Labelling

Aliquots of PNGase F-released N-glycans of fibrinogen were modified by either ethyl esterification or fluorescent labelling of the reducing end with 2-AA to allow for comparison between MALDI-TOF-MS and hydrophilic interaction liquid chromatography (HILIC) ultra high-performance liquid chromatography (UHPLC) with fluorescent detection. For ethyl esterification, the optimal conditions were established in previous experiments. 1 µL of fibrinogen release mix (24.12 µg protein) was added to 20 µL 0.25 M EDC 0.25 M HOBt in ethanol, and reacted for 1 h at 37° C. Subsequently, 20 µL ACN was added and the mixture stored at −20° C. for 15 min before glycan enrichment and MALDI-TOF-MS analysis.

For HILIC-UHPLC, the released N-glycans were labelled with 2-AA as described previously[33]. In short, 20 µL of PNGase F-released fibrinogen was mixed with 10 µL 2-AA (48 mg/mL) 15% glacial acetic acid in DMSO, and 10 µL 2-PB (107 mg/mL) in DMSO. The mixture was incubated for 2 h at 65° C. and diluted to 75% ACN before HILIC-UHPLC analysis.

Repeatability Testing

Repeatability of the established ethyl esterification conditions was ascertained by multiple analyses of the same sample across several days, performing all steps in a 96-well PCR plate (PP, Platte, Greiner Bio-One), sealing for incubation steps with adhesive tape (Nutacon, Leimuiden, Netherlands). For each day, 24 independent plasma samples were taken from the same pooled plasma, and deglycosylated with PNGase F as described before. 1 µL of each released sample was ethyl esterified by addition to a new PCR plate containing 20 µL 0.25 M HOBt 0.25 M EDC in ethanol, and incubated for 1 h at 37° C. After this, 20 µL ACN was added and the plate stored at −20° C. for 30 min. Samples were purified by cotton HILIC SPE and measured by MALDI-TOF-MS. The entire procedure was repeated twice in consecutive days with freshly prepared reagents to establish day-to-day variability.

HILIC SPE Glycan Enrichment

Glycan enrichment was performed by cotton HILIC SPE as described previously[32], with a few modifications. Samples removed from −20° C. were allowed to return to room temperature before proceeding. 20 µL pipette tips (Rainin Instrument, Oakland, US) were packed with 200 µg of cotton (HEMA, Netherlands), which was then conditioned by pipetting three times a volume of 20 µL MQ, and equilibrated with three times 20 µL 85% ACN. The sample was then loaded by pipetting 20 times into the reaction mixture. For pipetting the sample, care was taken not to include the precipitate, as clogging of the tip made the procedure more difficult. Performing the pipetting under an angle proved an easy way to prevent the precipitate from being disturbed, and yielded excellent results. The tips were washed three times with 20 µL 85% ACN 1% TFA, and three times with 20 µL 85% ACN. Subsequent elution was performed in 10 µL MQ. In case of a 96-wells plate format, a 12-channel pipette was used for all steps.

HILIC-UHPLC Measurement

Separation and analysis of 2-AA labelled N-glycans was carried out using HILIC-UHPLC with fluorescent detection. For this, a Dionex Ultimate 3000 (Thermo Fisher Scientific, Breda, Netherlands) was used with a 1.7 µm 2.1×100 mm Acquity UPLC BEH Glycan column (Waters). The column oven temperature was set to 60° C. and the flow rate to 0.6 mL/min. Two solutions were used for gradient generation, ACN as solution A, and 100 mM ammonium formate (prepared as FA buffered to pH 4.4 by NH4OH) as solution B. The samples were transferred using 75% solution A (the residual percentage always being solution B), and prior to separation the column was flushed with 85% A for 10 min. The flow gradient started at 75% A and decreased linearly to 57% A in 45 min. The column was then flushed again with 40% A for 10 min followed by 10 min of 85% A. Recorded chromatograms of fluorescence detection were analysed using Chromeleon version 7.1.2.1713 (Dionex).

MALDI-TOF-MS

For MALDI-TOF-MS analysis, 1 µL of glycan sample purified by cotton HILIC SPE was spotted on a MTP AnchorChip 800/384 TF MALDI target (Bruker Daltonik, Bremen, Germany), mixed on plate with 1 µL 2,5-DHB (5 mg/mL) in 50% ACN, and left to dry. Spotted like this, RP MALDI-TOF-MS spectra showed an almost 1:1 ratio of [M+Na]+ and [M+K]+ species, thereby complicating analysis. Adding 1 mM NaOH to the matrix solution corrected this problem, showing almost exclusively [M+Na]+ species.

The matrix crystals were homogenized by adding 0.2 µL ethanol, causing rapid recrystallization and thereby improving shot-to-shot reproducibility and decreasing salt adduction variability. Because spot crystallization was ultimately determined by the recrystallization step, spotted samples could initially be left to dry by air or rapidly dried under a flow of nitrogen without discernible differences to the spectra.

Analysis was performed by UltraFlextreme MALDI-TOF/TOF-MS (Bruker Daltonik, Bremen, Germany) in reflectron positive (RP) ion mode, using Flexcontrol 3.4 Build 119. Before sample measurement, the spectra were calibrated on the known masses of a peptide calibration standard (Bruker Daltonik, Bremen, Germany). All samples were ionized by a smartbeam-II laser, and accelerated with 25 kV after 140 ns delayed extraction. A mass window of m/z 100 to 1500 was used for α2,3- and α2,6-sialyllactose analysis, and for fibrinogen and plasma N-glycan samples a window of m/z 1000 to 5000 with suppression up to m/z 900. For each spectrum, 20000 laser shots were accumulated at a laser frequency of 2000 Hz, using a complete sample random walk with 200 shots per raster spot. High laser intensity was used for sample profiling to allow for ionization of larger glycan species, making sure the monoisotopic species was still clearly defined for all detectable masses.

Tandem mass spectrometry was performed on the most abundant peaks in human plasma N-glycome, using LIFT positive mode with laser induced disassociation.

Analysis of MALDI-TOF-MS Data

Using flexAnalysis v3.3 build 65 (Bruker Daltonik), the acquired MALDI-TOF-MS spectra were internally recalibrated using varying calibration masses. Abbreviations used for glycan annotation are: hexose (H), N-acetylhexosamine (N), fucose (F) and N-acetylneuraminic acid with unspecified linkage (S), with the accompanying number indicating the number of residues. Masses were calculated as [M+Na]+ for glycan compositions H3N4F1, H4N4F1, H5N4F1, H5N4S1, H5N4F1S1, H5N4S2, H6N5S3, H6N5F1S3 and H7N6S4, using different sialic acid masses depending on the derivatisation performed. For fibrinogen samples only the H5N4S1 and H5N4S2 masses were used for calibration, and for sialyllactose the H2S1 values were calculated for alkylated and lactonised sialic acid variants. Masses were picked in the spectra using a centroid algorithm using a mass window of 0.5 Da, followed by quadratic calibration. Recalibrated spectra were exported as text format and further analyzed using custom software. In short, analysis was performed as a targeted data extraction using a determined list of glycan compositions. For each composition, the isotope distribution was calculated, as well as the accompanying masses. For each isotope within 95% of the cumulative isotope cluster, the spectrum values were summed within a 1 Da mass window. Noise was then summed for a 1 Da region 1 Da lower than the isotope cluster and subtracted from each individual isotope (resulting in only the signal value). Observed isotopic ratios were compared to the calculated ones to prevent errors due to overlap, after which the individual isotope values were summed into one glycan composition value. The relative distribution of these glycan values was established within each spectrum, by dividing each value by the sum of all values. Averages and standard deviations of repeat experiments were calculated.

IgG Isolation

IgG was purified from healthy control plasma by employing Protein G Sepharose beads (GE Healthcare, Uppsala, Sweden). The beads were washed three times with 1×PBS and loaded on a low binding 350 μL MultiScreen filter plate (Millipore, Amsterdam, Netherlands) (15 μL beads per well), together with 150 μL 1×PBS. Two μL plasma was added to the beads in each well and incubated for 1 h on a shaking platform (600 RPM). The beads with attached IgGs were washed three times with 200 μL 1×PBS and three times with 200 μL MQ using a vacuum manifold. For elution, 100 μL 100 mM formic acid (Sigma-Aldrich) in MQ was added to the beads and the eluent was collected. Subsequently, the eluent was dried and resolved in 20 μL 50 mM ammonium bicarbonate (ABC) (Sigma-Aldrich). The isolated IgGs were stored at −20° C. until used.

IgG Digestion by Trypsin

Digestion of the isolated IgGs was performed by TPCK treated trypsin (Roche Diagnostics). To each well (containing approximately 20 μg IgG in 20 μL 50 mM ABC) 2 μg trypsin (1:10, enzyme:protein) was added and the plate was shaken for 10 min at 600 RPM. After confirming the pH to be between 6 and 10, the digestion mixture was incubated overnight at 37° C.

Bovine Fetuin

Bovine fetuin (Sigma-Aldrich) was dissolved to a concentration of 10.9 mg/mL in 25 mM ABC, of which 10 μL was subjected to PNGase F release. Ethyl esterification, cotton HILIC-SPE, and MALDI-TOF-MS analysis were carried out as previously described (FIG. 10A). MS/MS was performed to show the ethyl esterification and discrimination of sialic acids linked to N-acetylglucosamine residues (FIG. 10B).

Mouse Plasma N-Glycome

Mixed gender NaEDTA-buffered pooled plasma of mouse strain C57BL6 was acquired from Innovative Research (IMS-057BL6-N, Novi, Mich.). Twenty μL of this plasma was released by PNGase F, 1 μL of which was ethyl esterified, enriched for glycans by cotton HILIC-SPE, and analyzed by MALDI-TOF-MS (FIG. 11). MS/MS was performed to show the derivatisation of α2,3- and α2,6-linked N-glycolylneuraminic acids into lactones and ethyl esters (FIG. 12A), as well as the preservation of sialic acid O-acetylation by the ethyl esterification reaction (FIG. 12B).

Results

A robust, high-throughput MALDI-TOF-MS method for profiling human plasma N-glycans was developed with linkage-specific derivatisation of sialic acid residues. Reaction conditions were optimized to achieve ethylation for 2,6-linked sialic acid residues, whilst 2,3-linked sialic acid underwent lactone formation. Starting from 10 ul of human plasma, glycan profiles were achieved allowing the differentiation of 114 glycan species (FIG. 6). Method development and validation are described in the following.

Comparison of Different Activators/Reagents

A number of coupling reagents as well as combinations thereof were compared for linkage-specific methyl esterification of sialic acid residues in impure N-glycan mixtures. Commercially available pooled plasma (10 μl) was subjected to PNGase F treatment to obtain a complex sample with free N-glycans. Plasma N-glycome contains a large set of N-glycan compositions, including neutral as well as highly sialylated species with varying linkages [34, 35], and is therefore an informative sample to study the overall effects of a sialic acid modification methods. All reactions were performed directly on the unpurified PNGase F release mixture, using methanol as both methyl donor and solvent. Samples were reacted 1 h at 60° C. in methanol containing coupling/activation reagents DMT-MM, DCC, EDC, HOBt or Oxyma Pure, each with and without 0.2% TFA. Additionally, reagent combinations DCC+HOBt, DCC+Oxyma Pure, EDC+HOBt and EDC+Oxyma Pure were tried, each with and without 0.2% TFA. During the 1 h incubation step, white precipitate formed at the bottom of the samples, causing separation between the methanol soluble components within the mixture (which includes glycans and the coupling reagents), and the methanol insoluble fraction containing proteins.

Sample clean-up was deemed necessary for enrichment and purification of the glycans from the reaction mixture, and we chose for HILIC SPE using cotton as stationary phase as described previously[32]. A concentration between 25 and 75% ACN resulted in excellent retention without noticeable bias for low- or high-mass glycans, and the intermittent value of 50% ACN was chosen. The 1:1 mixture of the alcohol solution from the reaction and the ACN showed additional precipitate formation, so the samples was incubated 15 min at −20° C. to accelerate this process. To perform HILIC SPE, 200 µg of cotton was inserted into tips, washed with 3×20 µL MQ and 3×20 µL 85% ACN, loaded with sample by pipetting 20× into the reaction mixture, washed with 3×20 µL 85% ACN 1% TFA, 3×20 µL 85% ACN, and eluted with 10 µL MQ. Careful pipetting was necessary to prevent clotting of the tips.

1 µL of the purified samples was then spotted on an AnchorChip MALDI plate and co-crystallized with 1 µL 2,5-DHB (5 mg/mL) as matrix. To prevent potassium adduct formation, 1 mM NaOH was added to the matrix solution, yielding almost exclusively [M+Na]+ species. Recrystallization with was performed with 0.2 µL ethanol to decrease shot-to-shot variability, and further decrease the variety of salt adduction.

Effectiveness of the various reaction conditions was determined by taking into account the masses of the sialylated N-glycans, most notably H5N4S2, the most prominent glycan composition in plasma N-glycome (FIG. 1). The mass shift induced by the desired methyl esterification is +14.016 Da per sialic acid, resulting in a mass of 2273.804 Da [M+Na]+ for the fully esterified major plasma N-glycan H5N4S2. Unmodified sialic acids were only seen in RP mode when associated with an additional sodium (+21.982 Da per sialic acid), making signals at 2281.770 and 2289.736 indicative for incomplete reactions. In addition, lactonisation of one of the sialic acids could be observed, yielding an 18.011 Da mass loss, resulting in a signal at m/z 2241.777 [M+Na]+.

Single reagents DCC, EDC, HOBt and Oxyma Pure proved unable to modify sialic acids, regardless of whether acid was used during the reaction. DMT-MM did show methyl esterification of sialic acid residues, but also generated a prominent peak at m/z 2240.792 (−33.012 Da from the expected modified mass, overlapping with the lactonisation product), as well as amidation of carbonyl groups (−0.984 Da). These side-products were largely prevented by adding 0.2% TFA to the reaction, but strong acidic conditions may result in partial desialylation and loss of other labile substituents. Reagent combinations DCC+HOBt, DCC+Oxyma Pure and EDC+Oxyma pure each showed considerable methyl esterification of the sialic acid residues, but the presence of sodium adducts also indicated the conversion to be incomplete. This was largely, but not completely, corrected by acidic conditions. EDC+HOBt appeared to be the most promising reagent combination, showing complete conversion regardless of whether acid was used, and was therefore selected for further experimentation.

Testing of Different Alcohols

EDC+HOBt was selected as the most promising reagent mixture for sialic acid esterification, and various alcohols were tested in the following as combined precipitation agent and alkyl donor. Using 20 µL methanol, ethanol, 2-propanol and 1-butanol, 1 µL of plasma N-glycome solution was reacted 1 h at 60° C. 2-propanol and 1-butanol showed only to partly dissolve EDC and HOBt at room temperature, therefore a well-homogenized suspension was used. Purification, spotting and RP MALDI-TOF-MS measurement were performed as described above.

Analysis of sialylated glycan compositions showed all alcohols to be an alkyl group donor for sialic acid esterification (FIG. 2). Trisialylated glycan compositions H6N5S3 and H6N5F1S3 were studied as example. Expected masses after derivatisation with methanol, ethanol, 2-propanol and 1-butanol were 2944.047, 2986.094, 3028.141 and 3070.188 Da for composition H6N5S3, and 3090.105, 3132.152, 3174.199 and 3216.246 Da for H6N5F1S3 respectively, all observable in the recorded spectra. In addition, lactonisation products were present in all spectra, at mass differences of 32.026, 46.042, 60.058 and 74.073 Da, but relative ratios of the lactonised and alkyl esterified signals differed per alcohol. Isopropanol showed a large variety of reaction product in addition to the expected species, and isopropanol and 1-butanol both yielded relatively low signals for the sialylated glycans. Methanol and ethanol were selected as most promising solvents and alcohol donors for linkage-specific sialic acid modification, and were used for further method development.

Achieving Linkage Specificity

The linkage-specificity of EDC+HOBt in combination with methanol and ethanol was studied using oligosaccharide standards with known sialic acid linkage type, namely 3'-sialyllactose (Neu5Ac($\alpha$2,3)Gal($\beta$1,4)Glc) and 6'-sialyllactose (Neu5Ac($\alpha$2,6)Gal($\beta$1,4)Glc), both with purities higher than 98%. To study in addition the temperature effect on linkage-specificity, the samples were reacted not only 1 h at 60° C., but also at 50° C., 37° C., 21° C. and 4° C. Purification, spotting and RP MALDI-TOF-MS measurements were performed as before.

Relative quantification was performed between the lactonised reaction products (638.190 Da in all conditions) and the methyl- and ethyl esterified products (670.217 and 684.232 Da respectively) (FIG. 3). Unmodified reaction product was not found (678.183 Da), indicating all sialic acids were either esterified or lactonised. $\alpha$2,6-linked sialic acids were shown to be highly susceptible to alkylation, as both methanol and ethanol generated a near complete esterification (FIG. 4). However, lactonisation of $\alpha$2,3-linked sialic acids in methanol displayed a temperature dependent conversion, with a lower amount of side reaction (methanol esterification) formed at lower temperatures. Using methanol, correct lactonisation ranged from only 53.9% (SD±1.5%) at 60° C. to 93.6% (SD±0.6%) at 4° C. An environment of ethanol however, showed a much higher preference for 2,3-linked sialic acid lactonisation, on average showing only 2.3% (SD±0.9%) side reaction (ethanol esterification) across all temperatures. Because of the near-complete difference between 3'- and 6'-sialyllactose reaction products, ethanol was selected as the superior solvent and donor for linkage-specific sialic acid modification by EDC+HOBt. Reaction conditions were set at 1 h at 37° C. for further experimentation, to allow for a controlled temperature condition that is readily available in most laboratories.

It was also possible to derivatise and analyse N-glycolylneuraminic acid containing species.

Sialic Acid Stability

The ratios of H5N4S1 and H5N4S2 glycans released from fibrinogen were determined by MALDI-TOF-MS after ethyl esterification, and compared with HILIC-UHPLC after 2-AA labelling. Triplicate analysis and relative quantification of the mono- and disialylated glycans showed highly comparable signals, averaging on 65.3% and 34.7% (SD±1.5%) for MALDI-TOF-MS and 66.4% and 33.6% (SD±0.2%) for the UHPLC measurements (FIG. 5). Standard deviation of the MALDI method was noticeably higher than with the UHPLC method, but still had a coefficient of variation (CV) of 4.3% for the smaller peak, and 2.3% for the larger. Ratios observed are the ratio of the major monosialylated and disialylated biantennary glycans as determined by mass spectrometry and UHPLC very similar and in agreement with literature (respectively 61.94% and 38.06% of the sialylated N-glycan distribution of fibrinogen) [36].

Reproducibility

Reproducibility of human plasma N-glycome profiling employing 1 h 37° C. EDC+HOBt ethyl esterification was demonstrated by multiple repeat analyses on three different days. Pooled plasma was divided in 24 separate samples, glycans were released with PNGase F, ethyl esterified, purified by cotton HILIC SPE and analysed by RP MALDI-TOF-MS. Glycan signals were integrated, normalized to the sum of intensities and the relative signals and standard deviations calculated. This protocol was performed for two additional days to account for the day-to-day variation.

Plasma profiles studied using the ethyl esterification protocol showed glycans [M+Na]+ ranging in mass from 1257.423 Da (H5N2) to 4727.640 Da (H10N9F1 with four lactonised sialic acids (abbreviated as L) indicating α2,3-linkage) (FIG. 6). In total 217 distinct isotope clusters could be detected in the spectra, 114 of which could be attributed to glycan compositions within a mass deviation below 0.05 Da (average mass deviation 0.012 Da), accounting for approximately 90% of total spectrum. The most commonly found signals that could not be assigned to a native glycan mass showed a mass that was 101.051 Da lower than the associated major glycan peaks, indicating a likely 0.2 A cross-ring fragmentation at the reducing end N-acetylglucosamine.

Figure 7A:
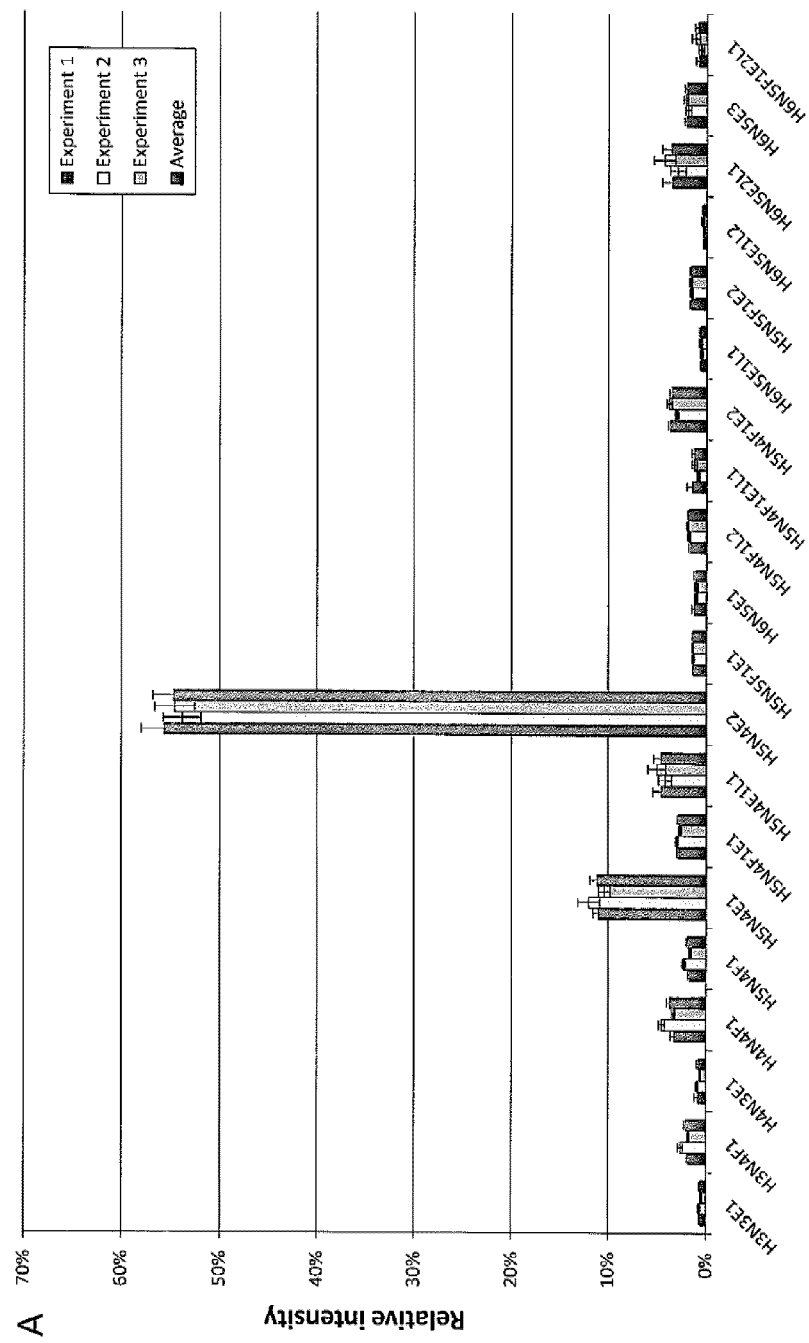
Figure 7B:
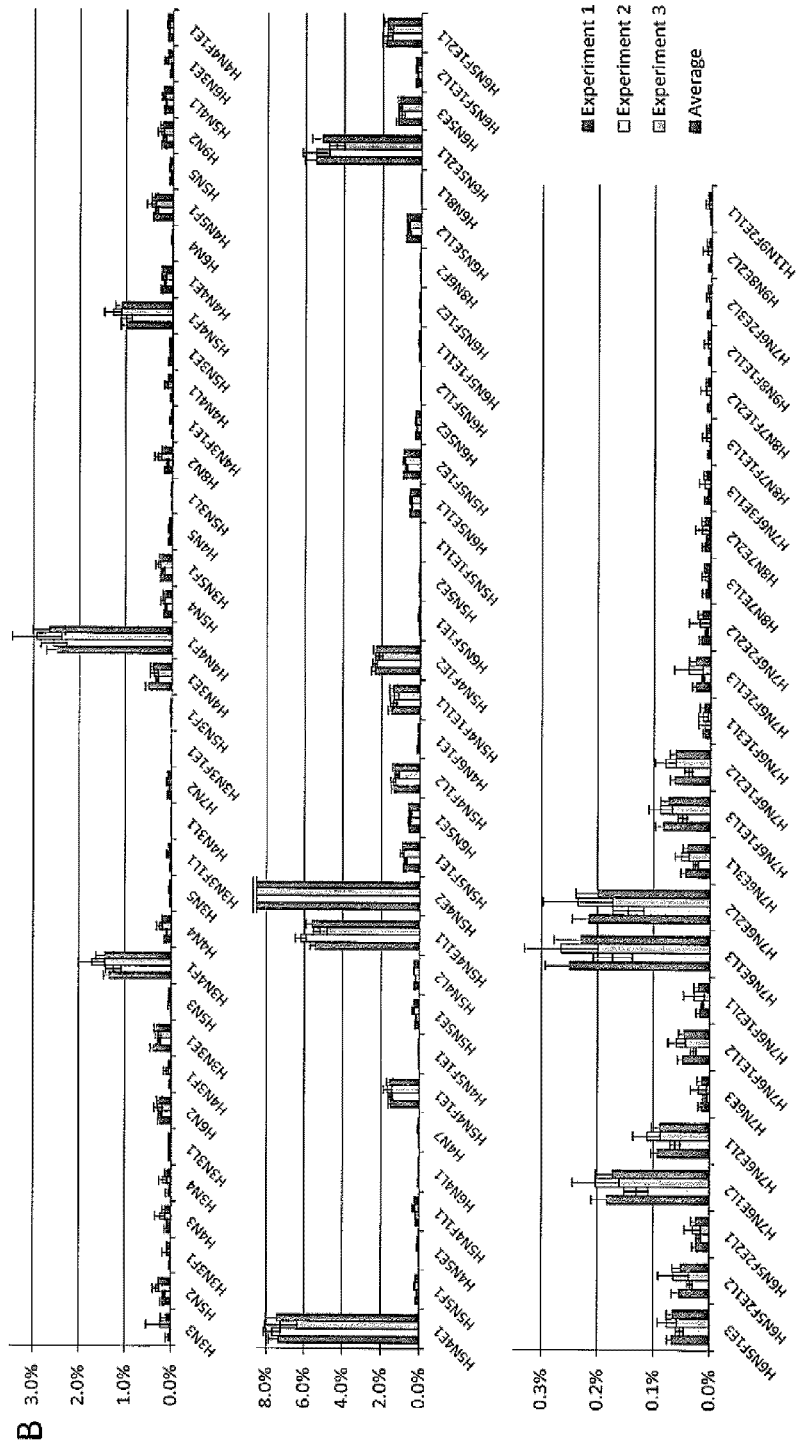

Repeatability analysis for the 20 highest abundant glycans (responsible for 94% of the cumulative glycan distribution of a spectrum) across 24 independent samples originating from the same plasma pool revealed high reproducibility within one batch, as well as between three batches prepared and measured on different days. Average relative intensity values for the highest peak (H5N4 with two esterified sialic acids (abbreviated as E) indicating α2,6-linkage) were around 54.7% (SD±2.3%) across all measurements, with the CV averaging around 3.8% (FIG. 7A). Analysis of all assigned glycan masses shows reasonable reproducibility even for values below 0.1% of the cumulative distribution (FIG. 7B).

Derivatisation of Reducing End Labelled N-Glycans

To test the ethyl esterification conditions for the derivatisation of reducing end labelled glycans, 2-aminobenzamide (2-AB) labelled A2F and A3 glycan standards were acquired from Ludger Ltd. (Abingdon, UK, product numbers CAB-A2F-01 and CAB-A3-01), and dissolved to 5 µM in MQ. One µL of these dissolved standards was added to 20 µL ethylation reagent, and subjected to 1 h incubation at 37° C. After 20 µL ACN addition, the glycans were recovered by cotton HILIC-SPE, and studied by MALDI-TOF-MS (FIG. 8).

Mass spectrometric assignments of the glycan compositions and sialic acid linkages are in agreement with the assignments performed by the vendor (HILIC HPLC profiling, exoglycosidase digestion). No signals were observed that could indicate side reactions due to the 2-AB label at the glycan reducing end, or incomplete reaction products.

Ig Digestion and Comparison of Alcohols for Glycopeptide Derivatisation

Based on the released glycan methodology, 0.25 M EDC and 0.25 M HOBt were together selected as the most promising carboxylic acid activators. Methanol and ethanol were used both as alkyl donor and solvent for the esterification reaction. For both conditions, 1 µL crude IgG digest was incubated with 20 µL reagent, and incubation was performed for 1 h at 37° C. (ethyl esterification) or 1 h at 4° C. (methyl esterification), conditions previously observed to give the highest linkage-specificity in reaction products. Hereafter, 20 µL ACN (50%, v/v) was added, the modified glycopeptides enriched from the reaction mixtures by cotton HILIC, and analysis performed by MALDI-TOF-MS (FIG. 9).

The present invention provides a number of distinct advantages over other prior art techniques for sialylated glycan derivatisation and analysis. For example, the reagents which have been developed display a high tolerance of sample impurities allowing sialic acid derivatisation of unenriched samples. There is also a high specificity of the reaction with regard to the sialic acid esterification, with a significant resistance to amidation, under- and overalkylation, as well as other side reactions. The mild reaction conditions employed prevent the loss of sialic acids and other labile groups. For example, acetylation of sialic acids may be preserved following derivatisation. The present invention therefore may find application in measuring the acetylation status of glycoproteins. This may be of use in analysing hormones which may be marketed and/or taken by subjects and could be of use, for example in drug characterisation and/or doping control—e.g. analysing erythropoietin.

Moreover, the speed and ease-of-use of the reagent (just add reagent and wait 15-60 min), its stability (12 weeks at −20° C.), low toxicity, very high linkage specificity between α2,3- and α2,6-linked sialic acids and compatibility with HILIC sample cleanup are further advantages.

Finally, the inventors have been able to observe very high masses in MALDI-TOF-MS profiling of PNGaseF-released plasma N-glycome (up to 4800 Da) and good reproducibility in profiling mode.

REFERENCE LIST

1. Wormald, M. R. and R. A. Dwek, *Glycoproteins: glycan presentation and protein-fold stability*. Structure, 1999. 7(7): p. R155-60.
2. Crocker, P. R., J. C. Paulson, and A. Varki, *Siglecs and their roles in the immune system*. Nature reviews. Immunology, 2007. 7(4): p. 255-66.
3. Muramatsu, T., *Essential roles of carbohydrate signals in development, immune response and tissue functions, as revealed by gene targeting*. Journal of biochemistry, 2000. 127(2): p. 171-6.
4. Adamczyk, B., T. Tharmalingam, and P. M. Rudd, *Glycans as cancer biomarkers*. Biochimica et biophysica acta, 2012. 1820(9): p. 1347-53.
5. van Kooyk, Y. and G. A. Rabinovich, *Protein-glycan interactions in the control of innate and adaptive immune responses*. Nature immunology, 2008. 9(6): p. 593-601.
6. Guillard, M., et al., *Plasma N-glycan profiling by mass spectrometry for congenital disorders of glycosylation type II*. Clinical chemistry, 2011. 57(4): p. 593-602.

7. Parekh, R. B., et al., *Association of rheumatoid arthritis and primary osteoarthritis with changes in the glycosylation pattern of total serum IgG*. Nature, 1985. 316 (6027): p. 452-7.
8. Dennis, J. W., M. Granovsky, and C. E. Warren, *Glycoprotein glycosylation and cancer progression*. Biochimica et biophysica acta, 1999. 1473(1): p. 21-34.
9. An, H. J., et al., *Glycomics and disease markers*. Current opinion in chemical biology, 2009. 13(5-6): p. 601-7.
10. Kawasaki, N., et al., *The significance of glycosylation analysis in development of biopharmaceuticals*. Biological & pharmaceutical bulletin, 2009. 32(5): p. 796-800.
11. Salles, G., et al., *Phase 1 study results of the type II glycoengineered humanized anti-CD20 monoclonal antibody obinutuzumab (GA101) in B-cell lymphoma patients*. Blood, 2012. 119(22): p. 5126-32.
12. Coggle, J. E. and J. P. Williams, *Experimental studies of radiation carcinogenesis in the skin: a review*. International journal of radiation biology, 1990. 57(4): p. 797-808.
13. Dall'Olio, F. and M. Chiricolo, *Sialyltransferases in cancer*. Glycoconjugate journal, 2001. 18(11-12): p. 841-50.
14. Schauer, R., *Sialic acids as regulators of molecular and cellular interactions*. Current opinion in structural biology, 2009. 19(5): p. 507-14.
15. Sperandio, M., C. A. Gleissner, and K. Ley, *Glycosylation in immune cell trafficking*. Immunological reviews, 2009. 230(1): p. 97-113.
16. Isozaki, H., T. Ohyama, and H. Mabuchi, *Expression of cell adhesion molecule CD44 and sialyl Lewis A in gastric carcinoma and colorectal carcinoma in association with hepatic metastasis*. International journal of oncology, 1998. 13(5): p. 935-42.
17. Nakayama, T., et al., *Expression of sialyl Lewis(a) as a new prognostic factor for patients with advanced colorectal carcinoma*. Cancer, 1995. 75(8): p. 2051-6.
18. Jeschke, U., et al., *Expression of sialyl lewis X, sialyl Lewis A, E-cadherin and cathepsin-D in human breast cancer: immunohistochemical analysis in mammary carcinoma in situ, invasive carcinomas and their lymph node metastasis*. Anticancer research, 2005. 25(3A): p. 1615-22.
19. Jorgensen, T., et al., *Up-regulation of the oligosaccharide sialyl LewisX: a new prognostic parameter in metastatic prostate cancer*. Cancer research, 1995. 55(9): p. 1817-9.
20. Schultz, M. J., A. F. Swindall, and S. L. Bellis, *Regulation of the metastatic cell phenotype by sialylated glycans*. Cancer metastasis reviews, 2012. 31(3-4): p. 501-18.
21. Zhuo, Y. and S. L. Bellis, *Emerging role of alpha2,6-sialic acid as a negative regulator of galectin binding and function*. The Journal of biological chemistry, 2011. 286 (8): p. 5935-41.
22. Hsu, D. K., R. Y. Yang, and F. T. Liu, *Galectins in apoptosis*. Methods in enzymology, 2006. 417: p. 256-73.
23. Harvey, D. J., *Matrix-assisted laser desorption/ionization mass spectrometry of carbohydrates*. Mass spectrometry reviews, 1999. 18(6): p. 349-450.
24. Powell, A. K. and D. J. Harvey, *Stabilization of sialic acids in N-linked oligosaccharides and gangliosides for analysis by positive ion matrix-assisted laser desorption/ionization mass spectrometry*. Rapid communications in mass spectrometry: RCM, 1996. 10(9): p. 1027-32.
25. Harvey, D. J., *Derivatization of carbohydrates for analysis by chromatography; electrophoresis and mass spectrometry*. Journal of chromatography. B, Analytical technologies in the biomedical and life sciences, 2011. 879 (17-18): p. 1196-225.
26. Ruhaak, L. R., et al., *Glycan labeling strategies and their use in identification and quantification*. Analytical and bioanalytical chemistry, 2010. 397(8): p. 3457-81.
27. Miura, Y., et al., *Rapid and simple solid-phase esterification of sialic acid residues for quantitative glycomics by mass spectrometry*. Chemistry, 2007. 13(17): p. 4797-804.
28. Wheeler, S. F., P. Domann, and D. J. Harvey, *Derivatization of sialic acids for stabilization in matrix-assisted laser desorption/ionization mass spectrometry and concomitant differentiation of alpha(2→3)- and alpha(2→6)-isomers*. Rapid communications in mass spectrometry: RCM, 2009. 23(2): p. 303-12.
29. Alley, W. R., Jr. and M. V. Novotny, *Glycomic analysis of sialic acid linkages in glycans derived from blood serum glycoproteins*. Journal of proteome research, 2010. 9(6): p. 3062-72.
30. Liu, X., et al., *Methylamidation for sialoglycomics by MALDI-MS: a facile derivatization strategy for both alpha2,3- and alpha2,6-linked sialic acids*. Analytical chemistry, 2010. 82(19): p. 8300-6.
31. Ruhaak, L. R., et al., *Hydrophilic interaction chromatography-based high-throughput sample preparation method for N-glycan analysis from total human plasma glycoproteins*. Analytical chemistry, 2008. 80(15): p. 6119-26.
32. Selman, M. H., et al., *Cotton HILIC SPE microtips for microscale purification and enrichment of glycans and glycopeptides*. Analytical chemistry, 2011. 83(7): p. 2492-9.
33. Ruhaak, L. R., et al., *2-picoline-borane: a non-toxic reducing agent for oligosaccharide labeling by reductive amination*. Proteomics, 2010. 10(12): p. 2330-6.
34. Knezevic, A., et al., *High throughput plasma N-glycome profiling using multiplexed labelling and UPLC with fluorescence detection*. The Analyst, 2011. 136(22): p. 4670-3.
35. Stumpo, K. A. and V. N. Reinhold, *The N-glycome of human plasma*. Journal of proteome research, 2010. 9(9): p. 4823-30.
36. Adamczyk, B., et al., *Characterization of fibrinogen glycosylation and its importance for serum/plasma N-glycome analysis*. Journal of proteome research, 2013. 12(1): p. 444-54.
37. Kornfeld, R. and S. Kornfeld, *Assembly of asparagine-linked oligosaccharides*. Annual review of biochemistry, 1985. 54: p. 631-64.
38. Nairn, A. V., et al., *Regulation of glycan structures in animal tissues: transcript profiling of glycan-related genes*. The Journal of biological chemistry, 2008. 283 (25): p. 17298-313.

The invention claimed is:

1. A method for derivatizing sialic acid residues present on glycan moieties by linkage specific alkyl esterification and lactone formation, the method comprising:
   reacting a biological sample or glycan preparation with an alcohol solution comprising a reagent comprising at least one carbodiimide(s) and at least one triazole or ethyl 2-cyano-2-(hydroxyimino)acetate (Oxyma pure), in order to derivatize any sialic acid residues present on glycan moieties present in the biological sample or glycan preparation.

2. The method according to claim 1 wherein acetylation of sialic acids is preserved with derivatization.

3. The method according to claim 1, wherein said at least one carbodiimide is N,N'-Dicyclohexylcarbodiimide (DCC), or 1 ethyl-3-(3-dimethyl amminopropyl) carbodiimide (EDC).

4. The method according to claim 1, wherein said triazole is hydroxybenzotriazole (HOBt).

5. The method according to claim 4 wherein hydroxybenzotriazole (HOBt) is in a hydrated form.

6. The method according to claim 1, wherein the reagent is a mixture, selected from the group consisting of DCC with HOBt, DCC with oxyma pure, EDC with HOBt and EDC with oxyma pure.

7. The method according to claim 1, wherein the alcohol is methanol, ethanol, (iso)propanol or butanol.

8. The method according to claim 7 wherein the alcohol is ethanol.

9. The method according to claim 1, wherein the method is carried out under acidic or neutral conditions.

10. The method according to claim 9 wherein the method is carried out in acidic conditions.

11. The method according to claim 10 wherein such acidic conditions are provided by the addition of 0.1%-0.4% trifluoracetic acid (TFA).

12. The method according to claim 1, wherein the method is carried out on pure or impure samples.

13. The method according to claim 12 wherein the impure sample is a biological sample.

14. The method according to claim 13 wherein the biological sample is a sample of plasma, immunoglobulin or fibrinogen which has been subjected to an enzymatic digestion.

15. The method according to claim 1, wherein the glycan moiety prior to or after derivatization is labelled with a radio or non-radioactive label isotope, or fluorescent or luminescent label.

16. The method according to claim 15 wherein the derivatized and labelled sialylated glycans are purified following derivatization and labelling by hydrophilic interaction chromatography (HILIC), porous graphitized carbon solid phase extraction (PGC-SPE), cationic exchange resins, liquid-liquid extraction or a mixture of the foregoing.

17. The method according to claim 1, wherein the derivatized sialylated glycans are purified following derivatization by hydrophilic interaction chromatography (HILIC) porous graphitized carbon solid phase extraction (PGC-SPE), cationic exchange resins, liquid-liquid extraction or a mixture of the foregoing.

18. The method according to claim 1, further comprising analysing the derivatized sialic acid residues present on the glycan moieties, by way of a suitable separation and detection of differentially linked sialic acids.

19. The method according to claim 18 wherein the derivatized sialic acid residues present on the glycan moieties are analysed by a mass spectrometric technique.

20. The method according to claim 19 wherein the mass spectrometric technique is MALDI-TOF analysis.

21. The method according to claim 20 wherein the derivatized sample is subjected to a recrystallisation step prior to the sample being analysed by MALDI-TOF.

22. The method according to claim 1 wherein the method detects and/or determines sialic acid acetylation and/or sialylation.

23. The method according to claim 1 wherein the sialic acid residues are linked to any monosaccharide.

24. The method according to claim 1 wherein the sialic acid residues are linked to either another sialic acid containing moiety, a hexose or N-acetylhexosamine.

25. A method of derivatizing sialic acid residues present on glycan moieties by linkage specific alkyl esterification and lactone formation, the method comprising:
    enzymatically treating a biological sample or glycan preparation in order to release glycan moieties present within the sample; and directly reacting the treated biological sample or glycan preparation with an alcohol solution comprising a reagent comprising at least one carbodiimide(s) and at least one triazole or ethyl 2-cyano-2-(hydroxyimino)acetate (Oxyma pure), in order to derivatize any sialic acid residues present on glycan moieties present in the biological sample or glycan preparation.

* * * * *